US012709775B2

(12) United States Patent
Gifford et al.

(10) Patent No.: US 12,709,775 B2
(45) **Date of Patent: *Aug. 18, 2026**

(54) METHODS FOR DISCOVERING AND USING LYMPHOCYTES WITH ANTIGEN SPECIFICITY

(71) Applicant: Think Therapeutics, Inc., Newton, MA (US)

(72) Inventors: David Kenneth Gifford, Newton, MA (US); Brandon Carter, Cambridge, MA (US)

(73) Assignee: Think Therapeutics, Inc., Newton, MA (US)

( * ) Notice: Subject to any disclaimer, the term of this patent is extended or adjusted under 35 U.S.C. 154(b) by 861 days.

This patent is subject to a terminal disclaimer.

(21) Appl. No.: 17/938,793

(22) Filed: Oct. 7, 2022

(65) Prior Publication Data

US 2023/0126286 A1 Apr. 27, 2023

Related U.S. Application Data

(60) Provisional application No. 63/262,974, filed on Oct. 25, 2021.

(51) Int. Cl.
*C12Q 1/6881* (2018.01)
*C12N 15/10* (2006.01)
*C12Q 1/6869* (2018.01)

(52) U.S. Cl.
CPC ....... *C12Q 1/6881* (2013.01); *C12N 15/1037* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 5,371,750 | A | 12/1994 | Inoue et al. |
| 8,691,510 | B2 | 4/2014 | Faham et al. |
| 9,708,654 | B2 | 7/2017 | Hunicke-Smith et al. |
| 10,066,265 | B2 | 9/2018 | Klinger et al. |
| 10,077,478 | B2 | 9/2018 | Faham et al. |
| 10,168,328 | B2 | 1/2019 | Berka |
| 10,539,564 | B2 | 1/2020 | Berka et al. |
| 11,111,489 | B1 | 9/2021 | Gifford et al. |
| 11,261,490 | B2 | 3/2022 | Klinger et al. |
| 2012/0196762 | A1 | 8/2012 | Paradis |
| 2015/0025812 | A1 | 1/2015 | Paradis |
| 2016/0024493 | A1 | 1/2016 | Robins |
| 2017/0114406 | A1 | 4/2017 | Hansen et al. |
| 2018/0087109 | A1 | 3/2018 | Klinger et al. |
| 2018/0282808 | A1 | 10/2018 | Milla et al. |
| 2019/0025299 | A1 | 1/2019 | Vigneault et al. |
| 2019/0055607 | A1 | 2/2019 | Jayaprakash |
| 2020/0123597 | A1 | 4/2020 | Daniel |
| 2020/0354784 | A1 | 11/2020 | Goldfless et al. |
| 2021/0269792 | A1 | 9/2021 | Falconer et al. |
| 2021/0293812 | A1 | 9/2021 | Vigneault et al. |

OTHER PUBLICATIONS

Bell et al., "Dynamics-Based Peptide-MHC Binding Optimization by a Convolutional Variational Autoencoder: A Use-Case Model for CASTELO," Journal of Chemical Theory and Computation, Nov. 18, 2021, vol. 17, pp. 7962-7971.
Xiao et al., "In silico design of MHC class I high binding affinity peptides through motifs activation map," BMC Bioinformatics, published Dec. 31, 2018, vol. 19(Suppl 19):516. 12 pages.
Ashby, "W. Ross Ashby's Journal: Zato-coding", Sep. 22, 1960, pp. 6208-6222. 8 pages. (http://www.rossashby.info/journal/page/6208.html.).
Binladen et al., "The use of coded PCR primers enables high-throughput sequencing of multiple homolog amplification products by 454 parallel sequencing," PLoS One, Feb. 14, 2007, ;2(2):e197. 9 pages.
Bowyer et al., "Activation-induced markers detect vaccine-specific CD4+ T cell responses not measured by assays conventionally used in clinical trials," Vaccines, 6(3), 50, Jul. 31, 2018. 19 pages.
D'yachkov et al., "Cover-free families and superimposed codes: Constructions, bounds, and applications to cryptography and group testing," Proceedings of IEEE International Symposium on Information Theory, Jun. 24-29, 2001, Washington, DC. DOI: 10.1109/ISIT.2001.935980. 1 page.
De Simone et al., "Single Cell T Cell Receptor Sequencing: Techniques and Future Challenges," Frontiers in Immunology, Jul. 18, 2018, 9:1638. 7 pages.
Du et al., "Deterministic Designs and Superimposed Codes," Chapter 7, Combinatorial Group Testing and Its Applications, Series on Applied Mathematics: vol. 12, 2nd Edition, https://doi.org/10.1142/4252, Dec. 1999, pp. 133-162.

(Continued)

*Primary Examiner* — G. Steven Vanni
(74) *Attorney, Agent, or Firm* — Wilmer Cutler Pickering Hale and Dorr LLP

(57) ABSTRACT

Described herein is a method for determining a lymphocyte cell receptor chain sequence specific to a unique antigen, comprising: sorting a plurality of antigens into a plurality of reaction mixtures, wherein the sorting comprises adding a unique antigen of the plurality of antigens to a unique subset of the plurality of reaction mixtures such that two different unique antigens are not added to the unique subset; contacting each reaction with a biological sample comprising a plurality of lymphocytes; separating a target lymphocyte from a subset of the plurality of lymphocytes, wherein the target lymphocyte recognizes the unique antigen; after separating the target lymphocyte, sequencing nucleic acids of the target lymphocyte to obtain the lymphocyte receptor chain sequence, wherein the sequencing is performed by single-cell sequencing; and detecting the unique antigen, wherein the detecting comprises: computing a frequency of lymphocyte cells that express the lymphocyte receptor chain sequence.

19 Claims, 4 Drawing Sheets

Specification includes a Sequence Listing.

(56) References Cited

OTHER PUBLICATIONS

Du et al., "DNA Applications," Chapter 9, Combinatorial Group Testing and Its Applications, Series on Applied Mathematics: vol. 12, 2nd Edition, https://doi.org/10.1142/4252, Dec. 1999, pp. 177-193.
D'yachkov et al., "Superimposed Codes and Threshold Group Testing," In: Aydinian, H., Cicalese, F., Deppe, C. (eds) Information Theory, Combinatorics, and Search Theory. Lecture Notes in Computer Science, vol. 7777. Springer, Berlin, Heidelberg (2013). https://doi.org/10.1007/978-3-642-36899-8_25. pages 509-533.
D'yachkov et al., "Superimposed Distance Codes," Problems of Control and Information Theory (1989), vol. 18(4), pp. 237-250.
Emerson et al., "Immunosequencing identifies signatures of cytomegalovirus exposure history and HLA-mediated effects on the T cell repertoire," Nature Genetics, May 2017, 49(5), pp. 659-665 and Online Methods. 10 pages.
Ericson et al., "Superimposed Codes in Rn," IEEE Transactions on Information Theory (1988), vol. 34(4), pp. 877-880. Aug. 1988. DOI: 10.1109/18.9789.
Furedi et al., "An improved upper bound of the rate of Eucledian superimposed codes," IEEE Transactions on Information Theory, Nov. 6, 1997, vol. 45(2), pp. 1-9.
Huang et al., "A Note on Decoding of Superimposed Codes," Journal of Combinatorial Optimization (2004), Dec. 2003, vol. 7, pp. 381-384.
International Search Report and Written Opinion mailed Jun. 8, 2022 in the International Application PCT/US2022/011275. 23 pages.
Kautz et al., "Nonrandom binary superimposed codes," IEEE Transactions on Information Theory, Oct. 1964, vol. 10(4), pp. 363-377. DOI: 10.1109/TIT.1964.1053689.
Kim et al., "Multi-error correcting codes for a binary asymmetric channel," IRE Transactions on Circuit Theory, May 1959, 6(5), 71-78.
Kivioja et al., "Counting absolute numbers of molecules using unique molecular identifiers," Nature Methods, Nov. 20, 2011, 9(1):72-74 and Online Methods. 5 pages.
Klinger et al., "Combining next-generation sequencing and immune assays: A novel method for identification of antigen-specific T cells," PLoS One, Sep. 19, 2013, 8(9):e74231. 9 pages.
Klinger et al., "Multiplex identification of antigen-specific T cell receptors using a combination of immune assays and immune receptor sequencing," PLoS One, Oct. 28, 2015, 10(10), e0141561. 21 pages.
Lissina et al., "Priming of Qualitatively Superior Human Effector CD8+ T Cells Using TLR8 Ligand Combined with FLT3 Ligand," The Journal of Immunology (2016), 196(1), pp. 256-263, published online Nov. 25, 2015. 9 pages.
Lugosch, "Learning Algorithms for Error Correction," Masters Thesis, McGill University, Apr. 2018. 82 pages. (https://lorenlugosch.github.io/Masters_Thesis.pdf).
Macula, "A simple construction of d-disjunct matrices with certain constant weights," Discrete Mathematics, Dec. 25, 1996, vol. 162, Issues 1-3, pp. 311-312. https://doi.org/10.1016/0012-365X(95)00296-9.
Mooers, "Zatocoding applied to mechanical organization of knowledge," American documentation, Jan. 1951, 2(1), 20-32. doi: 10.1002/asi.5090020107.
Nolan et al., "A large-scale database of T-cell receptor beta (TCRß) sequences and binding associations from natural and synthetic exposure to SARS-CoV-2," Research Square [Preprint]. Aug. 4, 2020. 28 pages. (https://doi.org/10.21203/rs.3.rs-51964/v1).
Reiss, et al., "Comparative analysis of activation induced marker (AIM) assays for sensitive identification of antigen-specific CD4 T cells," PLoS One, Oct. 24, 2017, 12(10), e0186998. 22 pages.
Rosenberg et al., "Single-cell profiling of the developing mouse brain and spinal cord with split-pool barcoding," Science, Apr. 13, 2018, 360(6385):176-182. 8 pages.
Ruszinko, "On the upper bound of the size of the r-cover-free families," Journal of Combinatorial Theory Series A, May 1994, vol. 66, issue 2, pp. 1-9.
Scheid et al., "A method for identification of HIV gp140 binding memory B cells in human blood," Journal of Immunological Methods (2009) 343(2), pp. 65-67. Available online Dec. 25, 2008.
Singh et al., "High-throughput targeted long-read single cell sequencing reveals the clonal and transcriptional landscape of lymphocytes," Nature Communications Jul. 16, 2019, 10(1):3120. 13 pages.
Snyder et al., "Magnitude and Dynamics of the T-Cell Response to SARS-CoV-2 Infection at Both Individual and Population Levels," medRxiv [Preprint]. Sep. 17, 2020. 33 pages.
Stahlberg et al., "Simple multiplexed PCR-based barcoding of DNA for ultrasensitive mutation detection by next-generation sequencing," Nature Protocols, Apr. 2017, 12(4), pp. 664-682.
Stubbington et al., "T cell fate and clonality inference from single-cell transcriptomes," Nature Methods, Apr. 2016, 13(4), pp. 329-332 and Online Methods. 7 pages.
Tapia-Calle et al., "A PBMC-Based System to Assess Human T Cell Responses to Influenza Vaccine Candidates In Vitro," Vaccines, Nov. 13, 2019, 7(4):181. 26 pages.
Zimmermann et al., "Antigen Extraction and B Cell Activation Enable Identification of Rare Membrane Antigen Specific Human B Cells," Frontiers in Immunology, Apr. 16, 2019, 10:829. 18 pages.
Zong et al., "Genome-wide detection of single-nucleotide and copy-number variations of a single human cell," Science, Dec. 21, 2012, 338(6114), pp. 1622-1626.

SEQUENCE LISTING

```
Sequence total quantity: 9
SEQ ID NO: 1           moltype = AA  length = 115
FEATURE                Location/Qualifiers
source                 1..115
                       organism = unidentified
                       mol_type = protein
                       note = VHH4
SEQUENCE: 1
QVQLQESGGG LVQAGGSLRL SCAASGSTLS SYGMGWYRQA PGKQREVVAT ISATGSISYA  60
DSVKGRFTIS RDSAKNTMYL QLNSLTPEDT AVYYCNTIYR STLYWGQGTQ VTVSS       115

SEQ ID NO: 2           moltype = AA  length = 146
FEATURE                Location/Qualifiers
source                 1..146
                       organism = unidentified
                       mol_type = protein
                       note = VHH7 protein sequence
SEQUENCE: 2
AQVQLVESGG GLVQAGDSLR LSCAASGRTF SRGVMGWFRR APGKEREFVA IFSGSSWSGR  60
STYYSDSVKG RFTISRDNAK NTVYLQMNGL KPEDTAVYYC AAGYPEAYSA YGRESTYDYW  120
GQGTQVTVSS EPKTPKPQPA RQACTS                                       146

SEQ ID NO: 3           moltype = AA  length = 10
FEATURE                Location/Qualifiers
source                 1..10
                       organism = synthetic construct
                       mol_type = protein
SEQUENCE: 3
GGSGGGGSGG                                                         10

SEQ ID NO: 4           moltype = AA  length = 9
FEATURE                Location/Qualifiers
source                 1..9
                       organism = synthetic construct
                       mol_type = protein
                       note = Seed: LVVVGADGV (SEQ ID NO: 5)
SEQUENCE: 4
LMVVGADGV                                                          9

SEQ ID NO: 5           moltype = AA  length = 9
FEATURE                Location/Qualifiers
source                 1..9
                       organism = Homo sapiens
                       mol_type = protein
SEQUENCE: 5
LVVVGADGV                                                          9

SEQ ID NO: 6           moltype = AA  length = 13
```

-continued

```
FEATURE                Location/Qualifiers
source                 1..13
                       organism = synthetic construct
                       mol_type = protein
                       note = Seed: EYKLVVVGADGVG (SEQ ID NO: 7)
SEQUENCE: 6
EYKFVVFGSD GAG                                                   13

SEQ ID NO: 7           moltype = AA  length = 13
FEATURE                Location/Qualifiers
source                 1..13
                       organism = Homo sapiens
                       mol_type = protein
SEQUENCE: 7
EYKLVVVGAD GVG                                                   13

SEQ ID NO: 8           moltype = AA  length = 134
FEATURE                Location/Qualifiers
source                 1..134
                       organism = synthetic construct
                       mol_type = protein
SEQUENCE: 8
QVQLQESGGG LVQAGGSLRL SCAASGSTLS SYGMGWYRQA PGKQREVVAT ISATGSISYA  60
DSVKGRFTIS RDSAKNTMYL QLNSLTPEDT AVYYCNTIYR STLYWGQGTQ VTVSSGGSGG  120
GGSGGLMVVG ADGV                                                  134

SEQ ID NO: 9           moltype = AA  length = 157
FEATURE                Location/Qualifiers
source                 1..157
                       organism = synthetic construct
                       mol_type = protein
SEQUENCE: 9
QVQLQESGGG LVQAGGSLRL SCAASGSTLS SYGMGWYRQA PGKQREVVAT ISATGSISYA  60
DSVKGRFTIS RDSAKNTMYL QLNSLTPEDT AVYYCNTIYR STLYWGQGTQ VTVSSGGSGG  120
GGSGGLMVVG ADGVGGSGGG GSGGEYKFVV FGSDGAG                          157
```

METHODS FOR DISCOVERING AND USING LYMPHOCYTES WITH ANTIGEN SPECIFICITY

CROSS-REFERENCE TO RELATED APPLICATIONS

This application claims the benefit of and priority under 35 U.S.C. § 119(e) to U.S. Ser. No. 63/262,974 filed Oct. 25, 2021, the contents of which is hereby incorporated by reference in its entirety.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction of the patent document or the patent disclosure as it appears in the U.S. Patent and Trademark Office patent file or records, but otherwise reserves any and all copyright rights.

INCORPORATION BY REFERENCE

All documents cited herein are incorporated herein by reference in their entirety.

SEQUENCE LISTING

The instant application contains a Sequence Listing which has been submitted electronically in XML format and is hereby incorporated by reference in its entirety. The XML copy, created on Sep. 27, 2022, is named 2215269_00130US2_Sequence_Listing_as_Filed.xml and is 8,226 bytes in size.

TECHNICAL FIELD

The present invention relates generally to identification of lymphocyte receptors that are specific to target antigens. More particularly, the present invention relates to systems and methods of accurately identifying lymphocyte (e.g., B cell or T cell) receptor sequence chains that are specific to one or more antigens or peptides of interest.

BACKGROUND

Determining lymphocyte cell immune receptor sequences that recognize specific antigens is a complex process that results in many false positives and false negatives. U.S. Pat. Nos. 10,066,265 and 10,077,478 disclose methods for determining the sequence of one or more lymphocyte receptor chains specific to antigens of interest but fail to disclose systems and methods that can produce accurate lymphocyte receptor chain sequences (e.g., with low false positive/negative rates) specific to one or more target antigens. There exists a need for improved methods and assays for discovering lymphocyte receptor chain sequences that bind to specific antigens in pool-based detection formats and algorithms.

SUMMARY

In one aspect, the invention provides for a method for determining a T cell receptor chain sequence, or a portion thereof, specific for one or more antigens, the method comprising: sorting a plurality of first antigens into a plurality of reaction mixtures, wherein the sorting comprises adding a unique antigen of the plurality of first antigens to a unique subset of the plurality of reaction mixtures, and wherein two unique antigens are not added to any two identical subsets of the plurality of reaction mixtures, contacting each reaction mixture with a biological sample comprising a plurality of T cells, providing a condition for a first activated T cell in at least one reaction mixture of the plurality of reaction mixtures to expand in number such that a plurality of T cell clones is formed, contacting the plurality of T cell clones with a query antigen, separating a second activated T cell and a non-activated T cell from a subset of the plurality of reaction mixtures, wherein the second activated T cell recognizes the query antigen, sequencing nucleic acids of the second activated T cell to obtain the T cell receptor chain sequence, and detecting the unique antigen of the plurality of first antigens, wherein the unique antigen is specific for the T cell receptor chain sequence In some embodiments, separating the second activated T cell and the non-activated T cell is performed based on a marker, wherein the marker is selected from the group consisting of CD3, CD4, CD8, CD137, OX40, CD25, PD-L1, CD69, CD154, and a combination thereof. In some embodiments, the T cell receptor chain sequence comprises a receptor chain sequence pair, wherein the receptor chain sequence pair consists of an alpha chain sequence and a beta chain sequence. In some embodiments, the second activated T cell recognizes the query antigen by binding an MHC complex comprising the query antigen. In some embodiments, the sorting further comprises applying, using a processor, an error-correcting code configured to determine the unique subset of the plurality of reaction mixtures that the unique antigen is added to. In some embodiments, the error-correcting code is a superimposed code. In some embodiments, the detecting comprises applying, using a processor, a decoding algorithm, wherein the decoding algorithm is configured to detect the unique antigen specific for the T cell receptor chain sequence when the T cell receptor chain sequence is not substantially present in at least one reaction mixture of the unique subset of the plurality of reaction mixtures. In some embodiments, the decoding algorithm is a nearest neighbor algorithm. In some embodiments, the query antigen is different from any antigen of the plurality of first antigens. In some embodiments, separating the second activated T cell and the non-activated T cell from the subset of the plurality of reaction mixtures is performed using multimer sorting. In some embodiments, separating the second activated T cell and the non-activated T cell from the subset of the plurality of reaction mixtures is performed using fluorescence-based sorting. In some embodiments, separating the second activated T cell and the non-activated T cell from the subset of the plurality of reaction mixtures is performed using bead-based sorting. In some embodiments, a number of reaction mixtures corresponding to the unique subset of the plurality of reaction mixtures is a function of a number of expected unique antigens that are specific to the T cell receptor chain sequence. In some embodiments, the plurality of reaction mixtures comprises at least one control reaction mixture, wherein the control reaction mixture does not contain any antigens that are added to the biological sample. In some embodiments, the detecting further comprises computing a frequency of T cells that express the T cell receptor chain sequence.

In another aspect, the invention provides for a method for determining a T cell receptor chain sequence, or a portion thereof, specific for one or more antigens, the method comprising: adding a plurality of first antigens to a first reaction mixture, contacting the first reaction mixture with a biological sample comprising a plurality of T cells, providing a condition for a first activated T cell in the first reaction mixture to expand in number such that a plurality of T cell clones is formed, sorting a plurality of query antigens into a plurality of reaction mixtures, wherein the sorting comprises adding a first query antigen of the plurality of query antigens to a unique subset of the plurality of reaction mixtures, wherein two unique query antigens are not added to any two identical subsets of the plurality of reaction mixtures, and wherein the first query antigen is different from any antigen of the plurality of first antigens, contacting each reaction mixture of the plurality of reaction mixtures with a portion of the first reaction mixture comprising the plurality of T cell clones, separating a second activated T cell from a subset of the plurality of T cell clones, wherein the second activated T cell recognizes the first query antigen, sequencing nucleic acids of the second activated T cell to obtain the T cell receptor chain sequence, and detecting the first query antigen specific for the T cell receptor chain sequence.

In some embodiments, separating the second activated T cell from the subset of the plurality of T cell clones is performed based on a marker, wherein the marker is selected from the group consisting of CD3, CD4, CD8, CD137, OX40, CD25, PD-L1, CD69, CD154, and a combination thereof. In some embodiments, the T cell receptor chain sequence comprises a receptor chain sequence pair, wherein the receptor chain sequence pair consists of an alpha chain sequence and a beta chain sequence. In some embodiments, the second activated T cell recognizes the first query antigen by binding an MHC complex comprising the first query antigen. In some embodiments, the sorting further comprises applying, using a processor, an error-correcting code configured to determine the unique subset of the plurality of reaction mixtures that the first query antigen is added to. In some embodiments, the error-correcting code is a superimposed code. In some embodiments, the detecting comprises applying, using a processor, a decoding algorithm, wherein the decoding algorithm is configured to detect the first query antigen specific for the T cell receptor chain sequence when the T cell receptor chain sequence is not substantially present in at least one reaction mixture of the unique subset of the plurality of reaction mixtures. In some embodiments, the decoding algorithm is a nearest neighbor algorithm. In some embodiments, separating the second activated T cell from the subset of the plurality of T cell clones is performed using multimer sorting. In some embodiments, separating the second activated T cell from the subset of the plurality of T cell clones is performed using fluorescence-based sorting. In some embodiments, separating the second activated T cell from the subset of the plurality of T cell clones is performed using bead-based sorting. In some embodiments, a number of reaction mixtures corresponding to the unique subset of the plurality of reaction mixtures is a function of a number of expected query antigens that are specific to the T cell receptor chain sequence. In some embodiments, the plurality of reaction mixtures comprises at least one control reaction mixture, wherein the control reaction mixture does not contain any antigens that are added to the biological sample. In some embodiments, the detecting further comprises computing a frequency of T cells that express the T cell receptor chain sequence.

In another aspect, the invention provides for a method for determining a lymphocyte cell receptor chain sequence, or a portion thereof, specific for at least two unique antigens, the method comprising: sorting a plurality of antigens into a plurality of reaction mixtures, wherein the sorting comprises adding the at least two unique antigens of the plurality of antigens-to at least two unique subsets of the plurality of reaction mixtures such that the at least two unique antigens are not added to any two identical subsets of the plurality of reaction mixtures, and wherein the at least two unique subsets are configured to allow a detection of the at least two unique antigens that are specific to the lymphocyte cell receptor chain sequence, contacting each reaction mixture of the plurality of reaction mixtures with a biological sample comprising a plurality of lymphocytes, separating a target lymphocyte from a subset of the plurality of lymphocytes, wherein the target lymphocyte recognizes the at least two unique antigens of the plurality of antigens, sequencing nucleic acids of the target lymphocyte to obtain the lymphocyte cell receptor chain sequence, and detecting the at least two unique antigens that are specific to the lymphocyte cell receptor chain sequence.

In some embodiments, the lymphocyte is a T cell or a B cell. In some embodiments, separating the target lymphocyte is performed using multimer sorting. In some embodiments, the target lymphocyte is a T cell, and wherein separating the T cell is based on a marker selected from the group consisting of CD3, CD4, CD8, CD137, OX40, CD25, PD-L1, CD69, and CD154. In some embodiments, the lymphocyte cell receptor chain sequence comprises a receptor chain sequence pair, and wherein the receptor chain sequence pair consists of two components of a receptor of the target lymphocyte. In some embodiments, a number of reaction mixtures comprising the at least two unique subsets is a function of a number of expected antigens that are specific to the lymphocyte cell receptor chain sequence. In some embodiments, the plurality of reaction mixtures comprises at least one control reaction mixture, and wherein the control reaction mixture does not contain any antigens that are added to the biological sample. In some embodiments, the target lymphocyte recognizes the at least two unique antigens of the plurality of antigens by binding the at least two unique antigens of the plurality of antigens or by binding two or more molecular complexes comprising the at least two unique antigens of the plurality of antigens. In some embodiments, the detecting further comprises applying, by a processor, a nearest set decoding algorithm configured to determine the at least two unique antigens that are specific to the lymphocyte cell receptor chain sequence. In some embodiments, the detecting further comprises: applying, by a processor, a decoding algorithm, wherein the decoding algorithm is configured to detect the at least two unique antigens that are specific to the lymphocyte cell receptor chain sequence when the lymphocyte cell receptor chain sequence is not substantially present in at least one reaction mixture of the at least two unique subsets of the plurality of reaction mixtures. In some embodiments, comprising assigning a superimposed code to each antigen of the plurality of antigens, wherein the superimposed code is configured to allow a detection of the at least two unique antigens that are specific to the lymphocyte cell receptor chain sequence.

In another aspect, the invention provides for a method for determining a lymphocyte cell receptor chain sequence, or a portion thereof, specific for at least two unique antigens, the method comprising: sorting a plurality of antigens into a plurality of reaction mixtures, wherein the sorting comprises adding at the at least two unique antigens of the plurality of antigens to at least two unique subsets of the plurality of reaction mixtures such that the at least two unique antigens are not added to any two identical subsets of the plurality of reaction mixtures, and wherein the at least two unique subsets are configured to allow a detection of the at least two unique antigens that are specific to the lymphocyte cell receptor chain sequence, contacting each reaction mixture with a biological sample comprising a plurality of lymphocytes, separating a target lymphocyte from a subset of the plurality of lymphocytes, wherein the target lymphocyte reacts with the at least two unique antigens of the plurality of antigens, sequencing nucleic acids of the target lymphocyte to obtain the lymphocyte cell receptor chain sequence, and applying, using a processor, a nearest set decoding algorithm configured to detect specificity of the lymphocyte cell receptor chain sequence to the at least two unique antigens.

In some embodiments, the lymphocyte is a T cell or a B cell. In some embodiments, the lymphocyte cell receptor chain sequence comprises a receptor chain sequence pair, and wherein the receptor chain sequence pair consists of two components of a receptor of the target lymphocyte. In some embodiments, comprising contacting at least one reaction mixture of the plurality of reaction mixtures with a query antigen.

In another aspect, the invention provides for a method for determining a lymphocyte cell receptor chain sequence, or a portion thereof, specific to a unique antigen, the method comprising: sorting a plurality of antigens into a plurality of reaction mixtures, wherein the sorting comprises adding a unique antigen of the plurality of antigens to a unique subset of the plurality of reaction mixtures such that two different unique antigens are not added to the unique subset, contacting each reaction mixture of the plurality of reaction mixtures with a biological sample comprising a plurality of lymphocytes, separating a target lymphocyte from a subset of the plurality of lymphocytes, wherein the target lymphocyte recognizes the unique antigen, after separating the target lymphocyte, sequencing nucleic acids of the target lymphocyte to obtain the lymphocyte receptor chain sequence, wherein the sequencing is performed by single-cell sequencing, and detecting the unique antigen, wherein the detecting comprises: computing a frequency of lymphocyte cells that express the lymphocyte receptor chain sequence.

In some embodiments, the lymphocyte is a T cell or a B cell. In some embodiments, the target lymphocyte is a T cell, and wherein the T cell is separated based on a marker selected from the group consisting of CD3, CD4, CD8, CD137, OX40, CD25, PD-L1, CD69, CD154, or a combination thereof. In some embodiments, the lymphocyte cell receptor chain sequence comprises a receptor chain sequence pair, and wherein the receptor chain sequence pair consists of two components of a receptor of the target lymphocyte. In some embodiments, the detecting further comprises: computing a gene expression value of a gene of the target lymphocyte. In some embodiments, the plurality of reaction mixtures comprises at least one control reaction mixture, and wherein the control reaction mixture does not contain any antigens that are added to the biological sample. In some embodiments, the target lymphocyte recognizes the unique antigen by binding the unique antigen or by binding one or more molecular complexes comprising the unique antigen. In some embodiments, the detecting further comprises applying, by a processor, a nearest set decoding algorithm configured to determine the unique antigen that is specific to the lymphocyte receptor chain sequence. In some embodiments, the detecting further comprises: applying, by a processor, a decoding algorithm, wherein the decoding algorithm is configured to detect the one or more antigens that are specific to the lymphocyte receptor chain sequence when the lymphocyte cell receptor chain sequence is not substantially present in at least one reaction mixture of the unique subset of the plurality of reaction mixtures, and wherein the at least one reaction mixture comprises the one or more antigens.

In another aspect, the invention provides for a method for determining a lymphocyte receptor chain sequence, or a portion thereof, specific for at least one antigen, the method comprising: providing a biological sample comprising a plurality of lymphocytes, extracting a plurality of first antigen presenting cells from the biological sample, dividing the plurality of first antigen presenting cells into a plurality of first reaction mixtures, sorting a plurality of first antigens into the plurality of first reaction mixtures, wherein the sorting comprises adding a unique first antigen of the plurality of first antigens to a unique subset of the plurality of first reaction mixtures, and wherein two unique first antigens are not added to any two identical subsets of the plurality of first reaction mixtures, contacting each first reaction mixture with the biological sample, providing a condition for a first activated lymphocyte in at least one first reaction mixture of the plurality of first reaction mixtures to expand in number such that a plurality of lymphocyte clones is formed, extracting a plurality of second antigen presenting cells from the biological sample, adding the plurality of second antigen presenting cells into a second reaction mixture, adding a plurality of query antigens into the second reaction mixture, dividing the second reaction mixture into the plurality of first reaction mixtures to create a plurality of final reaction mixtures, separating a second activated lymphocyte and a non-activated lymphocyte from a subset of the plurality of final reaction mixtures, wherein the second activated lymphocyte recognizes a query antigen of the plurality of query antigens, sequencing nucleic acids of the second activated lymphocyte to obtain the lymphocyte receptor chain sequence, and detecting the unique first antigen of the plurality of first antigens, wherein the unique first antigen is specific for the lymphocyte receptor chain sequence.

In some embodiments, the lymphocyte is a T cell or a B cell. In some embodiments, HLA typing of the biological sample to determine a predicted display of at least one antigen of the plurality of first antigens by an MHC molecule present in the biological sample. In some embodiments, enriching the plurality of lymphocytes prior to sorting the plurality of first antigens into the plurality of first reaction mixtures. In some embodiments, enriching the plurality of lymphocytes after providing the condition for the first activated lymphocyte to expand in number and prior to extracting the plurality of second antigen presenting cells. In some embodiments, separating the second activated lymphocyte and the non-activated lymphocyte is performed based on a marker, wherein the marker is selected from the group consisting of CD3, CD4, CD8, CD137, OX40, CD25, PD-L1, CD69, CD154, and a combination thereof. In some embodiments, the second activated lymphocyte recognizes the query antigen by binding an MHC complex comprising the query antigen. In some embodiments, the sorting further comprises applying, using a processor, an error-correcting code configured to determine the unique subset of the plurality of first reaction mixtures that the unique first antigen is added to. In some embodiments, the error-correcting code is a collision free superimposed code configured to allow for detection of at least two unique first antigens specific for the lymphocyte receptor chain sequence. In some embodiments, the collision free superimposed code is determined by a random search method. In some embodiments, the collision free superimposed code consists of: a plurality of prefix codes, wherein a prefix code of the plurality of prefix codes is assigned to the unique first antigen of the plurality of first antigens, wherein the prefix code identifies an overlap set, wherein the prefix code is identical for more than one first antigen of the plurality of first antigens within the overlap set, and a plurality of suffix codes, wherein a suffix code of the plurality of suffix codes is assigned to the unique first antigen of the plurality of first antigens, wherein a combination of the prefix code and the suffix code is distinct for the unique first antigen. In some embodiments, the detecting comprises applying, using a processor, a decoding algorithm, wherein the decoding algorithm is configured to detect the unique first antigen specific for the lymphocyte receptor chain sequence when the lymphocyte receptor chain sequence is not substantially present in at least one reaction mixture of the unique subset of the plurality of first reaction mixtures. In some embodiments, the decoding algorithm is a nearest set algorithm. In some embodiments, the query antigen is different from any antigen of the plurality of first antigens. In some embodiments, separating the second activated lymphocyte and the non-activated lymphocyte from the subset of the plurality of final reaction mixtures is performed using multimer sorting. In some embodiments, separating the second activated lymphocyte and the non-activated lymphocyte from the subset of the plurality of final reaction mixtures is performed using fluorescence-based sorting. In some embodiments, separating the second activated lymphocyte and the non-activated lymphocyte from the subset of the plurality of final reaction mixtures is performed using bead-based sorting. In some embodiments, a number of reaction mixtures corresponding to the unique subset of the plurality of first reaction mixtures is a function of a number of expected unique first antigens that are specific to the lymphocyte receptor chain sequence. In some embodiments, the plurality of first reaction mixtures comprises at least one control reaction mixture, wherein the control reaction mixture does not contain any antigens that are added to the biological sample. In some embodiments, the detecting further comprises computing a frequency of lymphocytes that express the lymphocyte receptor chain sequence.

BRIEF DESCRIPTION OF THE DRAWINGS

The following figures depict illustrative embodiments of the invention.

DETAILED DESCRIPTION

Figure 1:
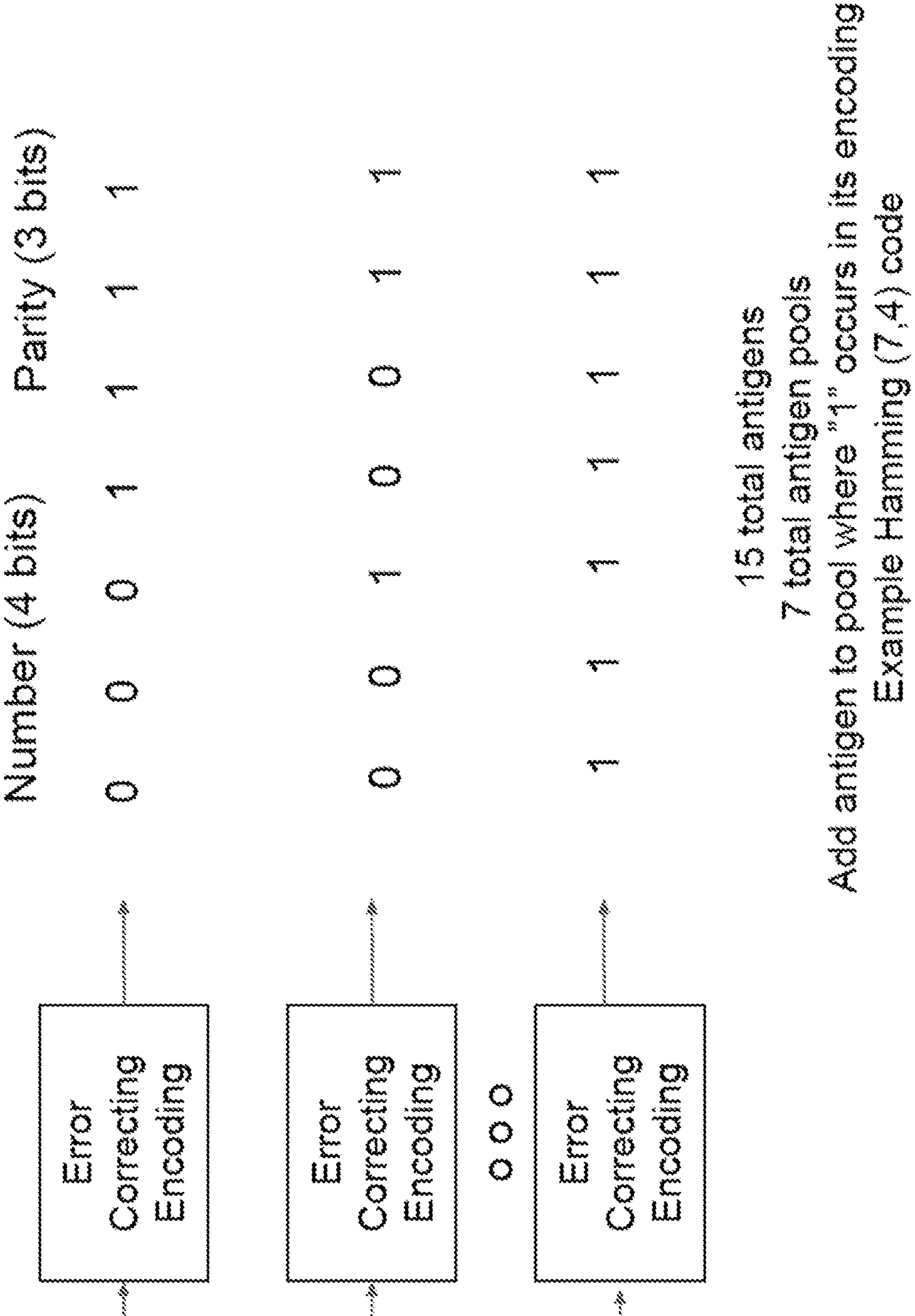
FIG. 1 illustrates a flow chart of multiplexing of antigens into samples using an error correcting code that detects errors during demultiplexing.

The systems and methods disclosed herein improve existing assays for discovering in pool-based formats the sequences of lymphocyte immune receptors that bind specific antigens directly or that bind molecular complexes (e.g., an MHC complex made of an MHC molecule and an antigen). This disclosure refers to the terms peptide(s) and antigen(s) interchangeably. In some embodiments, a "unique antigen" is an antigen with a specific amino acid sequence. In other embodiments, a "unique antigen" is an antigen derived from a specific epitope which can include multiple related peptides that are derived from that same epitope, and the "unique antigen" can therefore have more than one possible amino acid sequence. In some embodiments, a lymphocyte is an immune system cell (e.g., T cell or B cell) that displays a receptor. For example, a lymphocyte cell receptor (LCR) is an immune receptor molecule that is present on a lymphocyte (e.g., a T cell receptor or a B cell receptor). In some embodiments, a lymphocyte receptor chain sequence means the sequence of a portion of a receptor molecule that is most variable (e.g., a CDR3 region). In some embodiments, a lymphocyte receptor sequence pair is the two chain sequences of an immune receptor's two components (e.g., for a T cell receptor, it is the alpha and beta chain sequence, for a B cell receptor it is the heavy and light chain sequence). A lymphocyte recognizes an antigen when at least one of the lymphocyte's receptors binds the antigen, when at least one of the lymphocyte's receptors binds a complex that includes an antigen (e.g., MHC complex), or the lymphocyte is activated when its receptor binds the antigen.

One advantage of the present systems and methods relates to LCR promiscuity. Certain LCR chain sequences will recognize more than one antigen that are contained in different pools (also referred to as reaction mixtures herein). Thus, a LCR sequence discovery algorithm that depends on LCR chain sequences appearing in pools/reaction mixtures unique to one antigen may fail to produce accurate results. A second advantage of the present systems and methods relates to host lymphocyte activation and non-specific markers. Lymphocytes may display native activation markers when they are isolated from animals or patients in peripheral blood mononuclear cell (PBMC) samples, and thus their activation will not be a consequence of the assay antigens. A third advantage of the present systems and methods relates to experimental noise correction. The recognition of an antigen by a lymphocyte and its subsequent selection is imperfect as a consequence of experimental noise in the selection of antigen specific lymphocyte cells and their subsequent LCR sequencing. This can happen with weak lymphocyte cell activation by an antigen that results in few selected cells and correspondingly few or no observed LCR chain sequences in an expected pool. A fourth advantage of the present systems and methods relates to LCR chain sequence count calibration. The level of lymphocyte cell recognition of an antigen and sequence discovery will vary from assay to assay and person to person. Thus, a means to normalize LCR chain sequence counts from different assays using control antigens/peptides can facilitate their direct comparison. The present disclosure employs coding and antigen control pool to reduce assay errors introduced by LCR promiscuity, host lymphocyte cell activation, and experimental noise. It also provides LCR chain sequence count calibration to permit comparison of disparate assays.

In some embodiments, pooled assays are used to discover LCR chain sequences that correspond to LCRs displayed by lymphocyte cells that recognize a specific peptide/antigen. Referring to FIG. 1, K antigens (e.g., 15) are multiplexed into N antigen pools (e.g., 7), where N is less than K. K refers to the total number of antigens (or peptides) and N refers to the total number of antigen pools into which the K antigens (or peptides) are separated. Each antigen is added to a specific subset of pools, and when a LCR chain sequence (or a LCR chain sequence pair) of a lymphocyte that recognizes the antigen is observed to be enriched in this subset, a conclusion is drawn that the LCR chain sequence is specific for the antigen (or peptide). In some embodiments, antigens (or peptides) are placed into pools in a manner that allows the identification of LCRs on lymphocyte cells that recognize more than one antigen (or peptide). In some embodiments, antigens (or peptides) are encoded into pools such that LCR chain sequences corresponding to an antigen (or peptide) do not have to appear (or be detected) in all pools where the antigen (or peptide) was present. In some embodiments, the ability to detect LCRs that recognize antigens (or peptides) without having all corresponding pools that contain the antigen be recognized by lymphocytes with the LCR, improves the sensitivity and accuracy of the assay.

As shown in FIG. 1, the method begins by distributing a plurality of antigens (also referred to as peptides herein) into a plurality of antigen pools. In some embodiments, antigens (e.g., antigen 1 to antigen 15 as show in FIG. 1) are distributed into pools based on a minimum Hamming distance between the binary encoding of antigen pools where they reside. Antigens (peptides) are given numbers from 1 to K (e.g., 1 to 15), and each antigen (peptide) number is encoded into N bits (e.g., each bit labeled as 0 or 1), where N is the total number of antigen pools. The N bit encoding of an antigen number may be called its code word. FIG. 1 shows an example of 15 antigens (or peptides) that are each encoded into 7 bits (of 0s and 1s), where 7 is the number of antigen pools. An antigen is placed/distributed into a given antigen pool if the bit corresponding to that antigen pool is labeled "1" in the encoding of its number, and the peptide is not placed/distributed into a given antigen pool if the bit corresponding to that antigen pool is labeled "0", as shown in FIG. 1. In some embodiments, the encoding of the antigen number uses an error correcting code, such as a Hamming code, to enforce a minimum distance in bit changes between the encodings of two antigen numbers. In some embodiments, the distance between two encodings as measured by the number of bit differences is called the Hamming distance. FIG. 1 shows the use of a "Hamming(7,4)" code that encodes 15 peptides into 7 bit code words (corresponding to 7 antigen pools) resulting in a minimum Hamming distance of 3 (i.e., 4 data bits, 3 parity bits, and 7 total bits corresponding to 7 antigen pools). In some embodiments, code words which do not place an antigen into at least one pool (i.e., all zeros) are not used. Thus FIG. 1 does not utilize the all zero code word from the Hamming(7,4) code. The use of an error correcting code can improve the sensitivity of the assay by not requiring detection of an LCR chain sequence from a lymphocyte that recognizes an antigen in every pool where the antigen is present. This can arise when, for example, by chance some pools have a small number of lymphocytes that recognize an antigen (e.g., due to imperfect separation at step 203 of FIG. 2). The use of an error correcting code improves the accuracy of the assay by allowing the detection in a biological sample of a LCR chain sequence from a lymphocyte that recognizes an antigen in one or more pools where the antigen is not present (i.e., false positive). The use of an error correcting code also improves the accuracy of the assay by allowing the lack of detection in a biological sample of a LCR chain sequence from a lymphocyte that recognizes an antigen in one or more pools where the antigen is present (i.e., false negative).

The method using the Hamming(7,4) code depicted in FIG. 1 assumes that each LCR chain sequence will be enriched in a manner specific to one antigen of the 15 antigens. In some embodiments, codes for asymmetric channels can be used when the chance of a "1" occurring by error is higher than the chance of a "0" occurring by error. In some embodiments, codes for asymmetric channels can be used when the chance of a "0" occurring by error is higher than the chance of a "1" occurring by error. In some embodiments, a "1" occurs more often than a "0" when the separation of lymphocytes based on various markers is imperfect (i.e., false positive; e.g., occurring at step 203 of FIG. 2). In some embodiments, a "0" occurs more often than a "1" when there are a small number of lymphocyte cells that recognize an antigen (or peptide), and thus certain pools may have an insufficient number of lymphocyte cells that recognize an antigen (or peptide) to generate a "1" signal (i.e., false negative). In some embodiments, a "1" occurs more often than a "0" not due to error or chance, but rather when a lymphocyte cell recognizes more than one antigen (or peptide), and thus produces hits in pools associated with both antigens (or peptides). Examples of asymmetric codes that can perform error detection and correction optimally under these circumstances can be found in Kim and Freiman (1959), incorporated by reference in its entirety herein.

Following the assignment/sorting of peptides or antigens into antigen pools, the antigen pools are exposed to a tissue sample (e.g., PBMCs) to cause antigen pool specific antigens to be exposed to the lymphocytes contained in the tissue sample. In some embodiments, after exposure to the tissue sample, lymphocyte cells are activated by the antigens and then separated into activated and non-activated cells, and optionally also separated by other markers, as described in greater detail below. In some embodiments, after exposure to the tissue sample, lymphocyte cells bind the antigens and are then separated into antigen bound and non-bound cells, and optionally also separated by other markers, as described in greater detail below.

Figure 2:
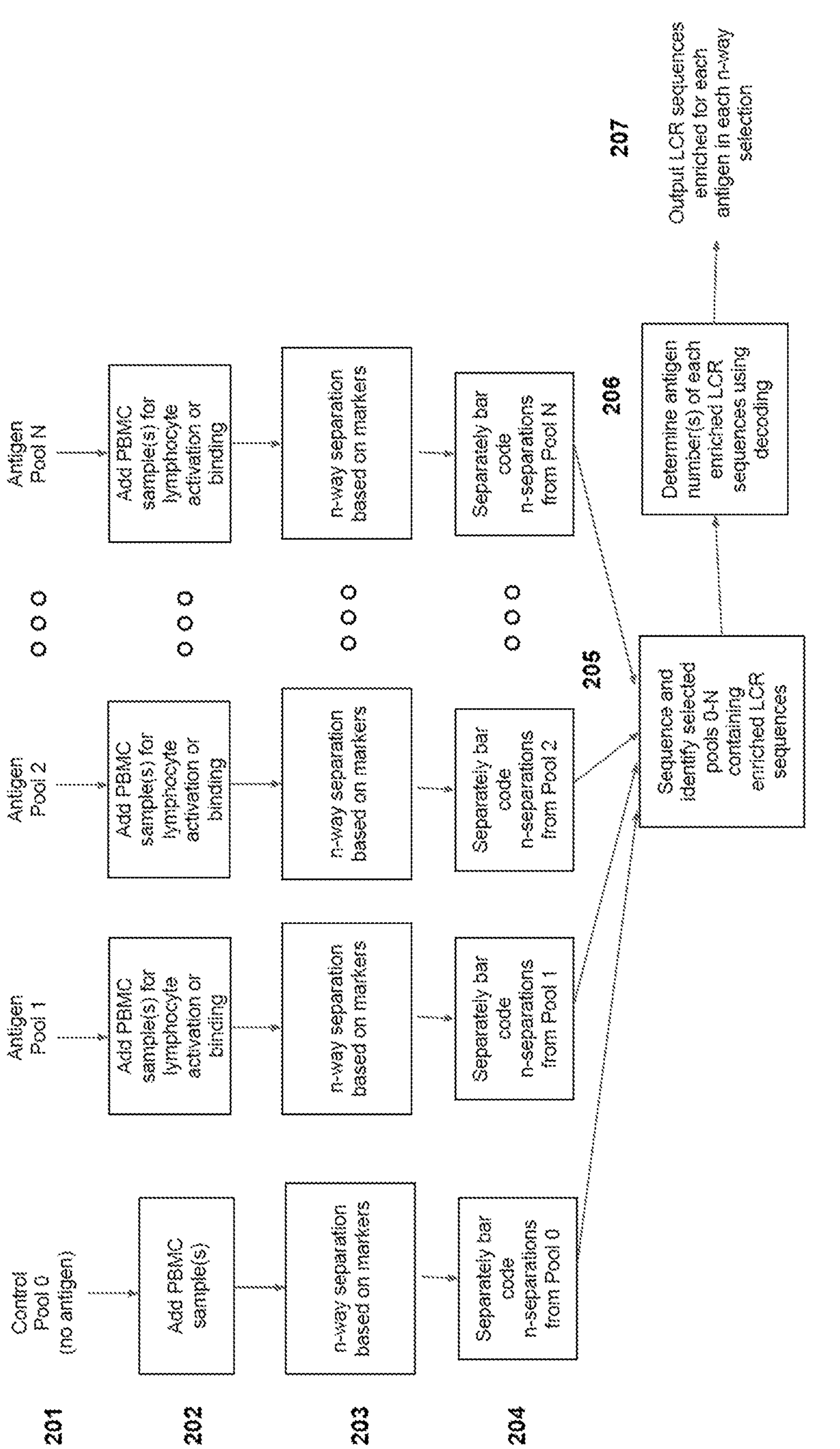
FIG. 2 illustrates a flow chart of detection of lymphocytes specific to antigens.

Referring to FIG. 2, the method begins at step 201 in which antigens (e.g., peptides) are separated into a plurality of antigen pools (e.g., antigen pool 1 to antigen pool N) using the methods described herein (e.g., see FIG. 1). In some embodiments, step 201 further includes creating a control pool ("Control Pool 0" in FIG. 2), which is free of added peptides/antigens (but may include peptides/antigens endogenous to a tissue sample, for example at step 201). At step 202, tissue samples (e.g., PBMCs) are separately exposed to the antigen pools. In some embodiments, the same tissue sample is split equally so that each antigen pool and the control pool are exposed to substantially the same tissue sample (e.g., with the same number and distribution of lymphocytes).

In some embodiments, lymphocytes that are activated by the antigen pools are allowed time to expand. In some embodiments, the antigen pools are separately re-stimulated with a query set of one or more antigens to test if the expanded lymphocytes respond to the query set of antigens. An example protocol that stimulates T cells with a first set of antigens and then queries with a second set of antigens is described by Tapia-Calle et al. (2019) "A PBMC-Based System to Assess Human T Cell Responses to Influenza Vaccine Candidates In Vitro." Vaccines (Basel). 2019 Nov. 13; 7(4):181, which is incorporated by reference in its entirety herein. In some embodiments, LCR chain sequences that correspond to lymphocytes that recognize the query antigens are determined using the pool based methods described herein. In some embodiments, each query antigen is assigned to the same pool as a pre-determined corresponding original pool antigen. In some embodiments, when a first plurality of antigens in the antigen pools are different than the query antigens, this assay permits the identification of lymphocyte clones that recognize both sets of antigens. For example, an increase in the frequency of a LCR chain sequence in a subset of the antigen pools in which a first antigen was added means that the LCR chain sequence is specific to that first antigen (since the corresponding lymphocytes were allowed time to expand, resulting in increased frequencies of the LCR sequence in corresponding antigen pools). A query antigen is then added to the same set of antigen pools matched to a first antigen. If the same LCR chain sequence is detected in an activated set of lymphocytes from the same group of antigen pools, a conclusion can be drawn that the LCR chain sequence recognizes both the first antigen and the query antigen. In some embodiments, query antigens are employed to test if a proposed derivative of a natural peptide, included as a first antigen, will cause expansion of lymphocyte clones that are activated by a query peptide (in which the query peptide is the natural peptide corresponding to the derivative of the natural peptide that was used as the first antigen). In some embodiments, self-peptides are employed as query antigens to test if proposed vaccine peptides (or antigens) in the first antigen pools activate lymphocytes that also are activated by self-peptides that are naturally found (e.g., query peptides are comprised of self-peptides).

In an alternative embodiment, a tissue sample (e.g., PBMCs) is exposed to a set of first antigens (e.g., peptides) to cause expansion of lymphocytes by the first set of antigens. The activated lymphocytes are allowed time to expand. The activated and expanded lymphocytes are then separated into pools that are stimulated with a second set of pool specific antigens (e.g., query peptides). Lymphocytes are separated into activated and non-activated cells, and optionally also separated by cell type. In some embodiments, this method is used to test which specific query antigens in the antigen pools are recognized by lymphocytes activated by the first set of antigens.

In some embodiments, adjuvants are added at step 201 when the tissue sample is exposed to antigens (e.g., prior to, simultaneously with, or following exposure to the antigens). One example method of using adjuvants is described in Lissina et al. (2016), "Priming of Qualitatively Superior Human Effector CD8+ T Cells Using TLR8 Ligand Combined with FLT3 Ligand" J Immunol. 2016 Jan. 1; 196(1): 256-263 incorporated by reference in its entirety herein. In some embodiments, antigen specific responses to the use of adjuvants are observed based on the enrichment of LCR chain sequences in specific antigen pools. In some embodiments, the adjuvants added at step 201 are molecules that provide co-stimulatory signals for lymphocytes (e.g., CD28 agonists, ICOS agonists, IL-2).

In some embodiments, at step 203, lymphocytes are separated by their binding of antigens, and optionally also separated by lymphocyte cell type or other markers. For example, methods of separating T cells based on the binding of their T cell receptors (TCRs) include MHC multimer (multimer) sorting, where a multimer displays a peptide in the context of an MHC molecule (see Klinger, et al., "Multiplex Identification of Antigen-Specific T Cell Receptors Using a Combination of Immune Assays and Immune Receptor Sequencing" PLoS One. 2015 Oct. 28; 10(10): e0141561). For each pool (e.g., pools 0 to/V), a set of fluorescent multimers is used that collectively displays all of the antigens (or peptides) present in a pool when bound by one or more than one MHC molecule. A given pool's cells are then sorted by cells that are specific to the multimers assigned to the pool by fluorescence activated cell sorting (FACS). In some embodiments, multi-parameter FACS is used to separate each cell by multimer positive and negative cells with the addition of one or more additional markers such as CD4+ (CD4+ T Cell), and CD8+ (CD8+ T Cell), or other desired markers. Methods of separating B cells include sorting B cells that are bound to an antigen in a pool, and optionally by their type as determined by cell surface markers or other means known in the art. Example methods of sorting B cells based on their binding of antigens are described in Scheid, et al., "A method for identification of HIV gp140 binding memory B cells in human blood" J Immunol Methods. 2009; 343(2):65-67 and Zimmermann, et al., "Antigen Extraction and B Cell Activation Enable Identification of Rare Membrane Antigen Specific Human B Cells" Front Immunol. 2019; 10:829, which are incorporated by reference herein in their entireties.

In some embodiments at step 203, lymphocytes are separated into activated and non-activated cells, and optionally also separated by cell type (e.g., T cell, T cell type). In some embodiments, at step 203, activation markers that are specific for activated cells, and/or different cell types, can be used to identify and then separate cells that are activated by an antigen. In some embodiments, antigens (peptides) are added to a PBMC sample and cells in the PBMC sample take up and display the antigens (peptides) using their native MHC molecules. Assays such as Activation Induced Markers (AIM) can be used to identify activation markers (see Bowyer et al. (2018). "Activation-induced markers detect vaccine-specific cd4+ t cell responses not measured by assays conventionally used in clinical trials" Vaccines, 6(3), 50 and Reiss S, et al., (2017) "Comparative analysis of activation induced marker (AIM) assays for sensitive identification of antigen-specific CD4 T cells" PLoS One, 12(10), e0186998, incorporated by reference in their entireties herein). Cell markers can be extracellular or intracellular, and cell permeabilization is used to permit antibodies to recognize intracellular markers. For example, activated T cells have been identified by their cell surface OX40+ CD25+ markers using AIM. The type of cell that is activated can be further discriminated with other activation markers, including CD3+ (CD3+ T Cell), CD4+ (CD4+ T Cell), and CD8+ (CD8+ T Cell). Other T cell activation markers known in the art can be used including CD137 and OX40, CD25, PD-L1, CD69, and CD154.

Lymphocyte cells can be physically separated by their markers at step 203 to enable the sequencing of the LCR chain sequences (at step 205, discussed in greater details below) in the physically separated cells. In some embodiments, four separations of T cells result from each pool at step 203: 1) CD8+, Activated, 2) CD8+, Not activated, 3) CD4+, Activated, and 3) CD4+, Not-activated.

Cell separation can be accomplished with bead-based methods, cell sorting-based methods, or other separation methods known in the art. Cell separation is accomplished at step 203. In some embodiments, cell separation can be two-way, four-way, or more ways. In some embodiments, one or more separations for each pool are retained. Markers used for separation can include cell proteins, antigen epitopes, antigens that are fluorescently tagged, fluorescent antibodies, florescent reagents, and other methods known in the art. Marker specific antibodies can be conjugated to beads, the beads can be exposed to a population of cells, and cells containing the selected markers can be physically separated by separating the beads. When selected cells are desired that are positive for more than one antibody, bead selections can be done serially. Alternatively, selection antibodies can be conjugated with a fluorescent dye and fluorescence activated cell sorting can be employed. In some embodiments, antigens are fluorescently tagged, and sorting can be accomplished using this as one marker. Multi-parameter flow sorting can permit the separation of cell based markers such as type (e.g., CD4, CD8) and their activation status at the same time. In some embodiments, all cell separations are retained for each antigen pool. In some embodiments, four separations of T cells result from each antigen pool: 1) CD8+, Activated, 2) CD8+, Not activated, 3) CD4+, Activated, and 4) CD4+, Not-activated.

At step 204, in some embodiments, nucleic acids are extracted from each separation of cells and separately amplified using TCR chain (e.g., T cell alpha, T cell beta, or both) or B cell receptor (BCR) chain (e.g., B cell heavy chain, B cell light chain, or both) specific PCR primers for sequencing. In some embodiments, DNA is extracted from each separation for sequencing. In some embodiments, RNA is extracted from each separation and converted into DNA by reverse transcription for sequencing. In some embodiments, control nucleic acid molecules that will be amplified with one or more of the specific PCR primers are added prior to PCR amplification to each separation at one or more predetermined concentrations to enable precise quantification of the number of LCR chain molecules present. Methods for sequencing TCR and BCR receptor sequences are described in U.S. Pat. No. 10,077,478, incorporated by reference in its entirety herein. In some embodiments, multiplex PCR is used to simultaneously amplify nucleic acid sequences originating from different LCR chains. In some embodiments, PCR primers encode bar codes that are contained in all of their product nucleic acid molecules as known in the art (Ståhlberg, et al., "Simple multiplexed PCR-based barcoding of DNA for ultrasensitive mutation detection by next-generation sequencing" Nat Protoc. 2017 April; 12(4):664-682, and Binladen, et al., "The use of coded PCR primers enables high-throughput sequencing of multiple homolog amplification products by 454 parallel sequencing" PLoS One. 2007 Feb. 14; 2(2):e197, incorporated by reference in their entireties herein). In some embodiments, PCR primers include Unique Molecular Identifiers (UMI) to provide more accurate counting of LCR chain molecules as known in the art (Kivioja, et al., "Counting absolute numbers of molecules using unique molecular identifiers" Nat Methods. 2011 Nov. 20; 9(1):72-4, incorporated by reference in its entirety herein). In some embodiments, when two or more reads contain the same UMI or random barcode (Ståhlberg, et al., 2017) and the same other contents, only one of the reads is counted. In some embodiments, the nucleic acids derived from separations from each pool include a separation specific bar-code when prepared for sequencing in step 204. In some embodiments, the amplified nucleic acids include a pool specific bar code to permit the mixing of pools for sequencing when prepared in step 204. In some embodiments, separate nucleic acid primers specific for LCR chains (e.g., alpha or beta) are used that include a chain specific bar code to amplify nucleic acids from each pool for sequencing in step 204. In some embodiments, molecules corresponding to amplified LCR chains contain a unique molecular identifier (UMI) and three bar codes: a separation specific bar code, an antigen pool specific bar code, and a LCR chain specific bar code (e.g., alpha or beta).

At step 204, in some embodiments, single-cell based methods are used to sequence LCR chains from one or more separations. In some embodiments, methods for measuring the RNA transcriptomes of single cells can provide paired sequences of LCR chains (De Simone, et al., "Single Cell T Cell Receptor Sequencing: Techniques and Future Challenges" Front Immunol. 2018 Jul. 18; 9:1638, Singh, et al., "High-throughput targeted long-read single cell sequencing reveals the clonal and transcriptional landscape of lymphocytes" Nat Commun. 2019 Jul. 16; 10(1):3120, Stubbington, et al., "T cell fate and clonality inference from single-cell transcriptomes" Nat Methods. 2016; 13(4):329-332, incorporated by reference in their entireties). In some embodiments, methods for sequencing the DNA of single cells can be used to produce LCR chain sequencing reads from single cells or a count of the number of cells that contain a LCR chain sequence (Zong, et al., "Genome-wide detection of single-nucleotide and copy-number variations of a single human cell" Science. 2012; 338(6114):1622-1626). In some embodiments, methods for measuring the RNA transcriptomes of single cells can be used that do not require the physical separation of single cells (Rosenberg, et al. "Single-cell profiling of the developing mouse brain and spinal cord with split-pool barcoding" Science. 2018 Apr. 13; 360 (6385):176-182). In some embodiments, methods that provide mRNA transcript levels from single cells can provide transcript levels for genes that indicate lymphocyte activation or other state information that can be used in addition to, or instead of, marker information to separate cells for analysis (Singh, et al. "High-throughput targeted long-read single cell sequencing reveals the clonal and transcriptional landscape of lymphocytes" Nat Commun. 2019 Jul. 16; 10(1):3120). In some embodiments, results from single-cell based methods are used in step 205 to determine, for each sequenced LCR chain, the pools in which it is enriched, as described herein. In some embodiments, the number of cells that contain an LCR chain sequence is used instead of LCR read counts in step 205. In some embodiments, mRNA transcript levels for genes from single-cell based methods are used to create or augment separations for desired analysis. Examples of mRNA expression markers include elevated expression of genes characteristic of active tissue resident cytotoxic lymphocytes, such as CCL4, NKG7, GZMA, and GZMK (Singh, et al. 2019). In some embodiments, expression or other sequencing derived markers from individual cells are used to augment or replace the separation labels (e.g., CD8+ Activated) associated with the physical separation of cells. In some embodiments, all or a portion of the cells in a pool can be analyzed by single-cell methods without separation by step 203.

At step 205, in some embodiments, the bar-coded separations are combined for sequencing on a high-throughput sequencer. The separations from each pool have their LCRs sequenced using high throughput sequencing technology. In some embodiments, adequate sequencing depth (number of raw reads from the sequencing instrument) is chosen by choosing a sequencing depth where the number of unique chains detected plateaus. At step 205, the sequencing reads from the bar-coded separations are then demultiplexed by their bar-codes for subsequent analysis. In some embodiments, decoding proceeds by identifying LCR chain sequences enriched in a desired set of physically separated pools, for example activated CD8+ cells. In some embodiments, LCR enrichment in a pool is determined by comparing LCR chain read counts observed in a desired separation (e.g., CD8+ Activated) to a function of the read counts observed in one or more other separations for the same pool (e.g., CD8+ Not activated, CD4+ Activated, CD4+ Not Activated). In some embodiments, LCR enrichment in a pool is determined by comparing LCR chain read counts observed in a desired separation (e.g., CD8+ Activated) to the read counts from one or more read counts of control nucleic acid molecules in one or more pools for the desired separation. In some embodiments, LCR enrichment in a pool is determined by comparing LCR chain read counts observed in a desired separation (e.g., CD8+ Activated) to a function of the read counts for one or more separations (e.g., CD8+ Activated) in one or more pools. In some embodiments, LCR enrichment in a pool is determined by comparing LCR chain read counts in a desired separation (e.g., CD8+, Activated) to a function of the read counts observed in one or more separations in Control Pool 0 (e.g., CD8+, Activated). In some embodiments, LCR enrichment in a pool is determined by computing a probability that the LCR chain read counts observed in a desired separation (e.g., CD8+ Activated) are drawn from a distribution computed using the read counts for one or more separations (e.g., CD8+ Activated) in one or more pools, and comparing this probability to a predetermined threshold (e.g., using standard deviation of a distribution). In some embodiments, LCR enrichment in a target pool is determined by computing the distribution of read counts observed in a desired separation (e.g., CD8+ Activated) in the target pool and comparing this distribution to one or more distributions of read counts observed in one or more separations (e.g., CD8+ Activated) in one or more other pools. In some embodiments, the enrichment of LCR chains in one or more pools is determined using statistical tests (e.g., Mann-Whitney U test, rank-sum test, Chi-squared test, t-test, ANOVA followed by post hoc tests) or other techniques known in the art when comparing to one or more alternative pools.

In some embodiments, LCR chain read counts are normalized in each pool by dividing by the total number of LCR chain read counts in complementary separations in that pool (e.g., for CD8+ Activated read counts: divide the CD8+ Activated read counts by the total CD8+ Activated plus CD8+ Not Activated read counts). In some embodiments, LCR chain read counts are normalized in each pool by dividing by the total number of LCR chain read counts in that pool. In some embodiments, for a desired separation (e.g., CD8+ Activated), the pool specific LCR chain read counts are normalized, and the normalized LCR chain read counts for that separation from all pools are clustered into two clusters using clustering methods known in the art (e.g., 2-means clustering). The cluster with the smaller average number of normalized read counts is labeled “0” and the cluster with the larger average number of normalized read counts is labeled “1”. In some embodiments, an LCR chain sequence in a specific pool and separation is assigned a “1” or “0” based on the label of its most likely cluster assignment. In some embodiments, an LCR chain sequence in a specific pool and separation is assigned a “1” or “0” based on the label of its most likely cluster assignment based on its maximum posterior probability assignment using Bayesian inference. In some embodiments, the LCR chain sequences assigned a “1” are considered to have been enriched.

In some embodiments, at step 205, LCR chain sequence enrichment in a pool is determined using the number of cells containing a given LCR chain sequence instead of the number of observed LCR chain sequence read counts as described herein. In single-cell analysis, sequencing reads include a cell specific bar code that permits the identification of the number of cells that contain a given LCR chain sequence. In some embodiments, when single cell RNA sequencing is employed, the number of observed sequencing reads will vary from cell-to-cell depending on the number of RNA molecules present in the cell that contain a LCR chain sequence. Thus, in some instances, cell counts provide a more accurate method of determining the number of cells that contain a LCR chain sequence. In some embodiments, specific cells that contain a LCR chain sequence can be identified with one or more desired markers. In some embodiments, when single-cell DNA sequencing is employed, variations and errors in the sequencing process that result in different numbers of observed LCR chain sequences for a given cell can be eliminated by using the number of cells that include a given LCR chain sequence (e.g., based on a predetermined threshold of LCR chain sequence detection in a given cell). In some embodiments, the number of cells containing a LCR chain sequence is used for analysis in steps 205-207 in place of read counts for each LCR chain sequence. In other embodiments, bulk sequencing methods are used for read counts which can still produce accurate results. In any embodiment of the present disclosure, read counts or cell counts may be used.

At step 206, for each unique LCR chain sequence that is enriched in at least one antigen pool, a binary number corresponding to the LCR chain sequence is determined corresponding to the antigen pools where it is enriched. In some embodiments, the method proceeds by decoding the binary number with the error correcting code used for encoding (e.g., see FIG. 1). In some embodiments, a nearest neighbor decoding algorithm as known in the art decodes the binary number into the antigen number with a corresponding code word with the smallest Hamming distance from the binary number. If there is more than one antigen code word with the same smallest distance, the decoding algorithm outputs an error. The result of decoding can be a valid antigen number, or it can represent an error. In some embodiments, the code used for decoding can detect errors when the pattern of enrichment does not correspond to a single antigen/peptide, and can correct errors when LCR chain sequence enrichment is corrupted by noise in samples up to the error correction limit of the code used. In some embodiments, a nearest set decoding algorithm as described herein decodes the binary number into one or more antigen numbers.

At step 207, the result of the methods described herein is the output of LCR sequences enriched for each antigen (e.g., peptide) in each antigen pool. In some embodiments, the decoding of antigen number(s) corresponding to an LCR chain sequence is based on the number of read counts of the LCR chain sequence in all pools, and these read counts are interpreted by a machine learning classifier (e.g., a neural network or other statistical model) that has been trained on examples of the code employed for placing antigens (peptides) in pools. An example of training a machine learning classifier for decoding an error correcting code is described in Lugosch, 2018, incorporated by reference in its entirety herein. In some embodiments, the decoding of the antigen number(s) corresponding to a LCR chain sequence is based on the number of reads of the LCR chain sequence in all pools, and a maximum a posteriori estimator of the best antigen number(s) for the LCR chain sequence is employed. In some embodiments, the method of the present disclosure includes any combination of one or more of steps 201-207. In some embodiments, unique TCR chain sequences corresponding to alpha and beta chains are independently decoded for a desired separation. In some embodiments, unique BCR chain sequences corresponding to BCR heavy and light chains are independently decoded for a desired separation.

In some embodiments, when the same antigen number is decoded for a TCR alpha and a TCR beta chain sequence, and only one alpha chain sequence and one beta chain sequence decodes into that antigen number, they are considered to have originated from the same TCR alpha-beta receptor sequence pair that is associated with that antigen. In some embodiments, all of the TCR alpha and TCR beta chain sequences that decode to the same antigen number are ranked in each pool by their read counts where one rank list is created for alpha chains, and one for beta chains. If a TCR alpha chain and a TCR beta chain sequence in each pool have the same pool specific rank order of read counts in the alpha and beta chain rank lists, they are considered to have originated from the same TCR alpha-beta receptor sequence pair. In some embodiments, single-cell sequencing methods are used to determine TCR alpha-beta receptor sequence pairs.

In some embodiments, when the same antigen number is decoded for a BCR heavy and a BCR light chain sequence, and only one light chain sequence and heavy beta chain sequence decodes into that antigen number, they are considered to have originated from the same BCR heavy-light receptor sequence pair that is associated with that antigen. In some embodiments, all of the BCR heavy and BCR light chain sequences that decode to the same antigen number are ranked in each pool by their read counts where one rank list is created for heavy chains, and one for beta chains. If a BCR heavy chain and a BCR light chain sequence in each pool have the same pool specific rank order of read counts in the heavy and light chain rank lists, they are considered to have originated from the same BCR heavy-light receptor sequence pair. In some embodiments, single-cell sequencing methods are used to determine BCR heavy-light receptor sequence pairs.

Non-Limiting Embodiments of the Subject Matter

In one aspect, the invention provides for a method for determining a T cell receptor chain sequence, or a portion thereof, specific for one or more antigens, the method comprising: sorting a plurality of first antigens into a plurality of reaction mixtures, wherein the sorting comprises adding a unique antigen of the plurality of first antigens to a unique subset of the plurality of reaction mixtures, and wherein two unique antigens are not added to any two identical subsets of the plurality of reaction mixtures, contacting each reaction mixture with a biological sample comprising a plurality of T cells, providing a condition for a first activated T cell in at least one reaction mixture of the plurality of reaction mixtures to expand in number such that a plurality of T cell clones is formed, contacting the plurality of T cell clones with a query antigen, separating a second activated T cell and a non-activated T cell from a subset of the plurality of reaction mixtures, wherein the second activated T cell recognizes the query antigen, sequencing nucleic acids of the second activated T cell to obtain the T cell receptor chain sequence, and detecting the unique antigen of the plurality of first antigens, wherein the unique antigen is specific for the T cell receptor chain sequence In some embodiments, separating the second activated T cell and the non-activated T cell is performed based on a marker, wherein the marker is selected from the group consisting of CD3, CD4, CD8, CD137, OX40, CD25, PD-L1, CD69, CD154, and a combination thereof. In some embodiments, the T cell receptor chain sequence comprises a receptor chain sequence pair, wherein the receptor chain sequence pair consists of an alpha chain sequence and a beta chain sequence. In some embodiments, the second activated T cell recognizes the query antigen by binding an MHC complex comprising the query antigen. In some embodiments, the sorting further comprises applying, using a processor, an error-correcting code configured to determine the unique subset of the plurality of reaction mixtures that the unique antigen is added to. In some embodiments, the error-correcting code is a superimposed code. In some embodiments, the detecting comprises applying, using a processor, a decoding algorithm, wherein the decoding algorithm is configured to detect the unique antigen specific for the T cell receptor chain sequence when the T cell receptor chain sequence is not substantially present in at least one reaction mixture of the unique subset of the plurality of reaction mixtures. In some embodiments, the decoding algorithm is a nearest neighbor algorithm. In some embodiments, the query antigen is different from any antigen of the plurality of first antigens. In some embodiments, separating the second activated T cell and the non-activated T cell from the subset of the plurality of reaction mixtures is performed using multimer sorting. In some embodiments, separating the second activated T cell and the non-activated T cell from the subset of the plurality of reaction mixtures is performed using fluorescence-based sorting. In some embodiments, separating the second activated T cell and the non-activated T cell from the subset of the plurality of reaction mixtures is performed using bead-based sorting. In some embodiments, a number of reaction mixtures corresponding to the unique subset of the plurality of reaction mixtures is a function of a number of expected unique antigens that are specific to the T cell receptor chain sequence. In some embodiments, the plurality of reaction mixtures comprises at least one control reaction mixture, wherein the control reaction mixture does not contain any antigens that are added to the biological sample. In some embodiments, the detecting further comprises computing a frequency of T cells that express the T cell receptor chain sequence.

In another aspect, the invention provides for a method for determining a T cell receptor chain sequence, or a portion thereof, specific for one or more antigens, the method comprising: adding a plurality of first antigens to a first reaction mixture, contacting the first reaction mixture with a biological sample comprising a plurality of T cells, providing a condition for a first activated T cell in the first reaction mixture to expand in number such that a plurality of T cell clones is formed, sorting a plurality of query antigens into a plurality of reaction mixtures, wherein the sorting comprises adding a first query antigen of the plurality of query antigens to a unique subset of the plurality of reaction mixtures, wherein two unique query antigens are not added to any two identical subsets of the plurality of reaction mixtures, and wherein the first query antigen is different from any antigen of the plurality of first antigens, contacting each reaction mixture of the plurality of reaction mixtures with a portion of the first reaction mixture comprising the plurality of T cell clones, separating a second activated T cell from a subset of the plurality of T cell clones, wherein the second activated T cell recognizes the first query antigen, sequencing nucleic acids of the second activated T cell to obtain the T cell receptor chain sequence, and detecting the first query antigen specific for the T cell receptor chain sequence.

In some embodiments, separating the second activated T cell from the subset of the plurality of T cell clones is performed based on a marker, wherein the marker is selected from the group consisting of CD3, CD4, CD8, CD137, OX40, CD25, PD-L1, CD69, CD154, and a combination thereof. In some embodiments, the T cell receptor chain sequence comprises a receptor chain sequence pair, wherein the receptor chain sequence pair consists of an alpha chain sequence and a beta chain sequence. In some embodiments, the second activated T cell recognizes the first query antigen by binding an MHC complex comprising the first query antigen. In some embodiments, the sorting further comprises applying, using a processor, an error-correcting code configured to determine the unique subset of the plurality of reaction mixtures that the first query antigen is added to. In some embodiments, the error-correcting code is a superimposed code. In some embodiments, the detecting comprises applying, using a processor, a decoding algorithm, wherein the decoding algorithm is configured to detect the first query antigen specific for the T cell receptor chain sequence when the T cell receptor chain sequence is not substantially present in at least one reaction mixture of the unique subset of the plurality of reaction mixtures. In some embodiments, the decoding algorithm is a nearest neighbor algorithm. In some embodiments, separating the second activated T cell from the subset of the plurality of T cell clones is performed using multimer sorting. In some embodiments, separating the second activated T cell from the subset of the plurality of T cell clones is performed using fluorescence-based sorting. In some embodiments, separating the second activated T cell from the subset of the plurality of T cell clones is performed using bead-based sorting. In some embodiments, a number of reaction mixtures corresponding to the unique subset of the plurality of reaction mixtures is a function of a number of expected query antigens that are specific to the T cell receptor chain sequence. In some embodiments, the plurality of reaction mixtures comprises at least one control reaction mixture, wherein the control reaction mixture does not contain any antigens that are added to the biological sample. In some embodiments, the detecting further comprises computing a frequency of T cells that express the T cell receptor chain sequence.

In another aspect, the invention provides for a method for determining a lymphocyte cell receptor chain sequence, or a portion thereof, specific for at least two unique antigens, the method comprising: sorting a plurality of antigens into a plurality of reaction mixtures, wherein the sorting comprises adding the at least two unique antigens of the plurality of antigens-to at least two unique subsets of the plurality of reaction mixtures such that the at least two unique antigens are not added to any two identical subsets of the plurality of reaction mixtures, and wherein the at least two unique subsets are configured to allow a detection of the at least two unique antigens that are specific to the lymphocyte cell receptor chain sequence, contacting each reaction mixture of the plurality of reaction mixtures with a biological sample comprising a plurality of lymphocytes, separating a target lymphocyte from a subset of the plurality of lymphocytes, wherein the target lymphocyte recognizes the at least two unique antigens of the plurality of antigens, sequencing nucleic acids of the target lymphocyte to obtain the lymphocyte cell receptor chain sequence, and detecting the at least two unique antigens that are specific to the lymphocyte cell receptor chain sequence.

In some embodiments, the lymphocyte is a T cell or a B cell. In some embodiments, separating the target lymphocyte is performed using multimer sorting. In some embodiments, the target lymphocyte is a T cell, and wherein separating the T cell is based on a marker selected from the group consisting of CD3, CD4, CD8, CD137, OX40, CD25, PD-L1, CD69, and CD154. In some embodiments, the lymphocyte cell receptor chain sequence comprises a receptor chain sequence pair, and wherein the receptor chain sequence pair consists of two components of a receptor of the target lymphocyte. In some embodiments, a number of reaction mixtures comprising the at least two unique subsets is a function of a number of expected antigens that are specific to the lymphocyte cell receptor chain sequence. In some embodiments, the plurality of reaction mixtures comprises at least one control reaction mixture, and wherein the control reaction mixture does not contain any antigens that are added to the biological sample. In some embodiments, the target lymphocyte recognizes the at least two unique antigens of the plurality of antigens by binding the at least two unique antigens of the plurality of antigens or by binding two or more molecular complexes comprising the at least two unique antigens of the plurality of antigens. In some embodiments, the detecting further comprises applying, by a processor, a nearest set decoding algorithm configured to determine the at least two unique antigens that are specific to the lymphocyte cell receptor chain sequence. In some embodiments, the detecting further comprises: applying, by a processor, a decoding algorithm, wherein the decoding algorithm is configured to detect the at least two unique antigens that are specific to the lymphocyte cell receptor chain sequence when the lymphocyte cell receptor chain sequence is not substantially present in at least one reaction mixture of the at least two unique subsets of the plurality of reaction mixtures. In some embodiments, comprising assigning a superimposed code to each antigen of the plurality of antigens, wherein the superimposed code is configured to allow a detection of the at least two unique antigens that are specific to the lymphocyte cell receptor chain sequence.

In another aspect, the invention provides for a method for determining a lymphocyte cell receptor chain sequence, or a portion thereof, specific for at least two unique antigens, the method comprising: sorting a plurality of antigens into a plurality of reaction mixtures, wherein the sorting comprises adding at the at least two unique antigens of the plurality of antigens to at least two unique subsets of the plurality of reaction mixtures such that the at least two unique antigens are not added to any two identical subsets of the plurality of reaction mixtures, and wherein the at least two unique subsets are configured to allow a detection of the at least two unique antigens that are specific to the lymphocyte cell receptor chain sequence, contacting each reaction mixture with a biological sample comprising a plurality of lymphocytes, separating a target lymphocyte from a subset of the plurality of lymphocytes, wherein the target lymphocyte reacts with the at least two unique antigens of the plurality of antigens, sequencing nucleic acids of the target lymphocyte to obtain the lymphocyte cell receptor chain sequence, and applying, using a processor, a nearest set decoding algorithm configured to detect specificity of the lymphocyte cell receptor chain sequence to the at least two unique antigens.

In some embodiments, the lymphocyte is a T cell or a B cell. In some embodiments, the lymphocyte cell receptor chain sequence comprises a receptor chain sequence pair, and wherein the receptor chain sequence pair consists of two components of a receptor of the target lymphocyte. In some embodiments, comprising contacting at least one reaction mixture of the plurality of reaction mixtures with a query antigen.

In another aspect, the invention provides for a method for determining a lymphocyte cell receptor chain sequence, or a portion thereof, specific to a unique antigen, the method comprising: sorting a plurality of antigens into a plurality of reaction mixtures, wherein the sorting comprises adding a unique antigen of the plurality of antigens to a unique subset of the plurality of reaction mixtures such that two different unique antigens are not added to the unique subset, contacting each reaction mixture of the plurality of reaction mixtures with a biological sample comprising a plurality of lymphocytes, separating a target lymphocyte from a subset of the plurality of lymphocytes, wherein the target lymphocyte recognizes the unique antigen, after separating the target lymphocyte, sequencing nucleic acids of the target lymphocyte to obtain the lymphocyte receptor chain sequence, wherein the sequencing is performed by single-cell sequencing, and detecting the unique antigen, wherein the detecting comprises: computing a frequency of lymphocyte cells that express the lymphocyte receptor chain sequence.

In some embodiments, the lymphocyte is a T cell or a B cell. In some embodiments, the target lymphocyte is a T cell, and wherein the T cell is separated based on a marker selected from the group consisting of CD3, CD4, CD8, CD137, OX40, CD25, PD-L1, CD69, CD154, or a combination thereof. In some embodiments, the lymphocyte cell receptor chain sequence comprises a receptor chain sequence pair, and wherein the receptor chain sequence pair consists of two components of a receptor of the target lymphocyte. In some embodiments, the detecting further comprises: computing a gene expression value of a gene of the target lymphocyte. In some embodiments, the plurality of reaction mixtures comprises at least one control reaction mixture, and wherein the control reaction mixture does not contain any antigens that are added to the biological sample. In some embodiments, the target lymphocyte recognizes the unique antigen by binding the unique antigen or by binding one or more molecular complexes comprising the unique antigen. In some embodiments, the detecting further comprises applying, by a processor, a nearest set decoding algorithm configured to determine the unique antigen that is specific to the lymphocyte receptor chain sequence. In some embodiments, the detecting further comprises: applying, by a processor, a decoding algorithm, wherein the decoding algorithm is configured to detect the one or more antigens that are specific to the lymphocyte receptor chain sequence when the lymphocyte cell receptor chain sequence is not substantially present in at least one reaction mixture of the unique subset of the plurality of reaction mixtures, and wherein the at least one reaction mixture comprises the one or more antigens.

In another aspect, the invention provides for a method for determining a lymphocyte receptor chain sequence, or a portion thereof, specific for at least one antigen, the method comprising: providing a biological sample comprising a plurality of lymphocytes, extracting a plurality of first antigen presenting cells from the biological sample, dividing the plurality of first antigen presenting cells into a plurality of first reaction mixtures, sorting a plurality of first antigens into the plurality of first reaction mixtures, wherein the sorting comprises adding a unique first antigen of the plurality of first antigens to a unique subset of the plurality of first reaction mixtures, and wherein two unique first antigens are not added to any two identical subsets of the plurality of first reaction mixtures, contacting each first reaction mixture with the biological sample, providing a condition for a first activated lymphocyte in at least one first reaction mixture of the plurality of first reaction mixtures to expand in number such that a plurality of lymphocyte clones is formed, extracting a plurality of second antigen presenting cells from the biological sample, adding the plurality of second antigen presenting cells into a second reaction mixture, adding a plurality of query antigens into the second reaction mixture, dividing the second reaction mixture into the plurality of first reaction mixtures to create a plurality of final reaction mixtures, separating a second activated lymphocyte and a non-activated lymphocyte from a subset of the plurality of final reaction mixtures, wherein the second activated lymphocyte recognizes a query antigen of the plurality of query antigens, sequencing nucleic acids of the second activated lymphocyte to obtain the lymphocyte receptor chain sequence, and detecting the unique first antigen of the plurality of first antigens, wherein the unique first antigen is specific for the lymphocyte receptor chain sequence.

In some embodiments, the lymphocyte is a T cell or a B cell. In some embodiments, HLA typing of the biological sample to determine a predicted display of at least one antigen of the plurality of first antigens by an MHC molecule present in the biological sample. In some embodiments, enriching the plurality of lymphocytes prior to sorting the plurality of first antigens into the plurality of first reaction mixtures. In some embodiments, enriching the plurality of lymphocytes after providing the condition for the first activated lymphocyte to expand in number and prior to extracting the plurality of second antigen presenting cells. In some embodiments, separating the second activated lymphocyte and the non-activated lymphocyte is performed based on a marker, wherein the marker is selected from the group consisting of CD3, CD4, CD8, CD137, OX40, CD25, PD-L1, CD69, CD154, and a combination thereof. In some embodiments, the second activated lymphocyte recognizes the query antigen by binding an MHC complex comprising the query antigen. In some embodiments, the sorting further comprises applying, using a processor, an error-correcting code configured to determine the unique subset of the plurality of first reaction mixtures that the unique first antigen is added to. In some embodiments, the error-correcting code is a collision free superimposed code configured to allow for detection of at least two unique first antigens specific for the lymphocyte receptor chain sequence. In some embodiments, the collision free superimposed code is determined by a random search method. In some embodiments, the collision free superimposed code consists of: a plurality of prefix codes, wherein a prefix code of the plurality of prefix codes is assigned to the unique first antigen of the plurality of first antigens, wherein the prefix code identifies an overlap set, wherein the prefix code is identical for more than one first antigen of the plurality of first antigens within the overlap set, and a plurality of suffix codes, wherein a suffix code of the plurality of suffix codes is assigned to the unique first antigen of the plurality of first antigens, wherein a combination of the prefix code and the suffix code is distinct for the unique first antigen. In some embodiments, the detecting comprises applying, using a processor, a decoding algorithm, wherein the decoding algorithm is configured to detect the unique first antigen specific for the lymphocyte receptor chain sequence when the lymphocyte receptor chain sequence is not substantially present in at least one reaction mixture of the unique subset of the plurality of first reaction mixtures. In some embodiments, the decoding algorithm is a nearest set algorithm. In some embodiments, the query antigen is different from any antigen of the plurality of first antigens. In some embodiments, separating the second activated lymphocyte and the non-activated lymphocyte from the subset of the plurality of final reaction mixtures is performed using multimer sorting. In some embodiments, separating the second activated lymphocyte and the non-activated lymphocyte from the subset of the plurality of final reaction mixtures is performed using fluorescence-based sorting. In some embodiments, separating the second activated lymphocyte and the non-activated lymphocyte from the subset of the plurality of final reaction mixtures is performed using bead-based sorting. In some embodiments, a number of reaction mixtures corresponding to the unique subset of the plurality of first reaction mixtures is a function of a number of expected unique first antigens that are specific to the lymphocyte receptor chain sequence. In some embodiments, the plurality of first reaction mixtures comprises at least one control reaction mixture, wherein the control reaction mixture does not contain any antigens that are added to the biological sample. In some embodiments, the detecting further comprises computing a frequency of lymphocytes that express the lymphocyte receptor chain sequence.

TCR Promiscuity

In some embodiments, superimposed codes are used to separate peptides/antigens into antigen pools at step 201 which allows the assay to detect which peptides/antigens are recognized by a single LCR chain sequence when it recognizes more than one peptide/antigen. An example of a superimposed code is a Zatocoding (see Mooers, C. N., and Ashby, W. R., 1951, incorporated by reference in its entirety herein).

In some embodiments, superimposed codes are applied to assign each antigen (e.g., peptide) to n antigen pools that are unique to the antigen. If N is the total number of antigen pools utilized, then a given antigen is assigned to a subset of these antigen pools n, where n<N. In some embodiments, preferably n is equal to F*N, where F is the fraction of antigen pools that are optimal. In some embodiments, the binary number corresponding to the pools that an antigen is assigned to is the code word of that antigen, where a pool in which it is present is assigned a "1" and a pool where it is absent is assigned a "0", and these binary digits are concatenated to form the antigen's code word (e.g., for five pools, inclusion in pools 1 and 3, and exclusion in pools 2, 4, and 5 would result in the binary number "10100"). The fraction of antigen pools F is typically $1\text{-}2^{-1/r}$ where r is the desired detection ability of a given TCR chain sequence to recognize r antigens. Table 1 provides the fraction, F, of the total number of antigen pools, N, that should be used for a given antigen according to the equation above.

TABLE 1

Number of antigens r by Fraction of antigen pools F

| r (Number of antigens expected to be recognized by a typical LCR) | F (Fraction of antigen pools assigned to each antigen) |
|---|---|
| 1 | .5 |
| 2 | .293 |
| 3 | .205 |
| 4 | .159 |

In some embodiments, each antigen (e.g., peptide) is randomly assigned to F*N antigen pools, except that it is ensured that no two antigens are allocated to exactly the same group of antigen pools. In some embodiments, an antigen's code word describes the pools in which it is present and absent, where "1" represents a pool where it is present and "0" represents a pool where it is absent. These binary digits are concatenated in pool number order (e.g., the antigen code word "01100" means the antigen is present in pools 2 and 3, and not present in pools 1, 4, and 5). In some embodiments, the assignment of antigens to antigen pools (e.g., their code words) is recorded. In some embodiments, for a LCR chain sequence observed in the sequencing of an antigen pool's desired positive selected component (e.g., CD8+ Activated), the sequence's enrichment is computed versus its presence in the sequencing data from the negative selection of this pool (e.g., CD8+ Not Activated). In some embodiments, for a LCR chain sequence observed in the sequencing of an antigen pool's desired positive selected component, the sequence's enrichment is computed versus its presence in the sequencing data from other antigen pools. In some embodiments, LCR chain sequence enrichment is computed based on read counts. In some embodiments, enrichment is computed based on read counts as corrected by UMIs. In some embodiments, LCR chain sequence enrichment is computed based on cell counts. In some embodiments, pool specific LCR chain sequence enrichment is computed as described herein.

In some embodiments, if a LCR chain sequence is enriched in a number of antigen pools that is larger than r*F*N, then the LCR chain sequence is flagged as recognizing more than r antigens. In some embodiments, for each antigen, the antigen pools it was assigned to are evaluated for enriched LCR chain sequences. In some embodiments, when all of the pools corresponding to an antigen's assignment are enriched for a LCR chain sequence as described herein, then the LCR chain sequence is output as recognizing the antigen. The false positive rate of the assay is expected to be bounded by $(1/2)^n$ when r is an accurate estimate. Thus, when n is more than about 3, the false positive rate should be small. In some embodiments, to reduce the error rate, N is increased which causes a corresponding increase in n to lower the false positive rate to a desired level. In some embodiments, collision free superimposed codes as described herein are utilized to ensure that every valid code word can be decoded into a single unique set of antigens. The receptor sequence pairing of LCR chain sequences (T cell alpha and beta, B cell heavy and light) is accomplished as described herein for paired chains that are assigned to the same antigen or antigens. Rank comparisons of read counts for pairing receptor chain sequences is done for each antigen separately.

In some embodiments, a binary number corresponding to the enrichment of a LCR chain sequence is constructed by concatenating its enriched ("1") and non-enriched ("0") pools (e.g., "10101" corresponds to a LCR chain sequence enriched in pools 1, 3, and 5, and not enriched in pools 2 and 4). The Hamming distance of this binary number is computed with respect to the result of the "OR" of the code words for each possible combination of the antigens. Described herein is a nearest set decoding algorithm which determines whether there is a unique nearest neighbor in Hamming distance between the binary number and a single antigen code word, or between the binary number the Boolean bit-wise "OR" of a combination of two or more antigen code words. When such a unique nearest neighbor in Hamming distance is found, the nearest set decoding algorithm outputs the corresponding combination of antigens as being recognized by the LCR chain sequence. For example, if there are K antigens, the method considers all 2K possible "OR" combinations of antigen code words, including single code words, all combinations of 2 code words, all combinations of 3 code words, and so on. This method allows decoding in situations where a LCR chain sequence is specific to more than one antigen (e.g., by computing a Hamming distance for a set of combined code words). In some embodiments, antigens are only considered in combinations if their code words have a minimum number of "1" bits that are also present in the binary number being decoded. In some embodiments, if there are K antigens, the method considers all $$\sum_{j=1}^{r} \binom{K}{j}$$

possible "OR" combinations of antigen code words from up to r antigens (where r is the number of antigens expected to be recognized by a typical LCR used during encoding). In some embodiments, other distance metrics (e.g., Euclidean distance, cosine distance) are used to compute nearest neighbors. In some embodiments, if there is not a unique nearest neighbor, the nearest set decoding method outputs an error.

Nearest Set Decoding Algorithm

In some embodiments, a nearest set decoding algorithm consists of the following computational steps.

In some embodiments, the inputs for the computation are:

N: Number of antigen pools.

K: Number of antigens.

$E_{1, \ldots, N}$: The observed enrichment (enriched: "1"; non-enriched: "0") of a LCR chain sequence in each of the N antigen pools.

$C_{1, \ldots, K}$: Matrix of code words for each of K antigens where $C_i$ specifies a binary number corresponding to the antigen pools where antigen i is present. The binary digits are concatenated in pool number order, where "1" represents a pool where the antigen is present, and "0" represents a pool where it is absent.

m: Threshold minimum number of antigen pools overlapping with the observed enrichment to consider an antigen for "OR" combinations during superimposed decoding.

Neighbor-Distance: A distance function (e.g., Hamming distance, Euclidean distance, cosine distance) used to compute the distance between two code words. This function takes in two code words represented as binary numbers and outputs an integer distance. In some embodiments, generalized minimum distance decoding or maximum likelihood decoding can be used for neighbor distance functions.

From the input pool enrichments $E_{1, \ldots, N}$, for a given LCR chain sequence, a corresponding binary number sequence B is constructed by concatenating the enriched ("1") and non-enriched ("0") pools for the LCR chain sequence. The binary digits are concatenated in pool number order, where "1" represents a pool where the LCR chain sequence is enriched, and "0" represents a pool where it is not enriched (e.g., B="10101" which corresponds to an LCR chain sequence enriched in pools 1, 3, and 5, and not enriched in pools 2 and 4).

Next, a set of basis code words W is computed for the purpose of decoding. In some embodiments, if antigens were distributed into antigen pools using an error-correcting code (e.g., a Hamming(7,4) code), then $W=U_iC_i$ (where W is the union of all code words in C and i is a given antigen). In some embodiments, if antigens were distributed into antigen pools using a superimposed code (e.g., a zatocoding; a collision free superimposed code), W is the union of all $2^K$ possible bit-wise Boolean "OR" combinations of antigen code words in C, including single code words, all combinations of 2 code words, all combinations of 3 code words, and so on, and each base code word in W is annotated by the combination of antigen code words used to create it. For example, if $C_1$ is "11000" and $C_2$ is "00101" then the combination of $C_1$ and $C_2$ would be represented by "11101" in W which is the bit-wise "OR" of the two code words, and "11101" would be annotated as the combination $C_1$ and $C_2$. In some embodiments, antigens are only considered in combinations if their code words have at least m "1" bits that are also present in B, the code word being decoded. In some embodiments, W does not include combinations of antigen code words for more than r antigens at once, and thus the number of possible "OR" combinations of antigen code words up to r antigens is $$\sum_{j=1}^{r} \binom{K}{j}$$

(where r is me number of antigens expected to be recognized by a typical LCR used during encoding). For each basis code word, W stores both the binary code word and its annotation of the one or more antigens that corresponds to the basis code word.

Next, the distances $d_1, \ldots, d_j$ between B and all basis code words 1, . . . , j in W are computed using the Neighbor-Distance function. For example, if the Neighbor-Distance function uses a Hamming distance, the Neighbor-Distance is the number of positions in a code word sequence in which the two code words differ. For N pools, a code word has N positions. For N=5, if B=00111 (first code word) and $W_1$=11000 (second code word), then $d_1$=5 (the maximum possible Hamming distance for N=5). If B=00111 (first code word) and $W_2$=00110 (second code word), then $d_2$=1. Let z be the minimum of $d_1, \ldots, d_j$. If there is not a unique distance with minimum distance z, the output will be an error ("ERROR"). Otherwise, the output will be the annotated basis antigen(s) in $W_i$ corresponding to basis code word $d_i$ with distance z. The output may consist of a single antigen or multiple antigens that were combined using "OR" to form basis code word $W_i$. If the output consists of multiple antigens, the LCR chain sequence is specific to more than one antigen.

Host T Cell Activation and Non-Specific Markers

In some embodiments, a separate control pool is established that contains no antigens/peptides ("Control Pool 0"; see FIG. 2). This pool is separated at step 203, as are the other pools, and is used to detect cells that are activated when they are retrieved from a donor. In some embodiments, donor cells are derived from humans or animals. LCR chain sequences that are found in the separated active set of cells in the control pool represent LCR chain sequences that correspond to host activated cells or cells that contain AIM markers that are not induced by the antigens/peptides in the other pools (i.e., the antigen pools). In some embodiments, these LCR chain sequences can be eliminated from the antigen specific set of LCR chain sequences discovered in the remainder of the antigen pools.

LCR Chain Sequence Count Calibration

In some embodiments, control antigens (e.g., control peptides) can be added to target antigens of interest to calibrate the assay across donors. Control antigens that are broadly present in the human population can be derived from common immunizations such as measles, mumps, rubella, polio, and other control antigens/peptides can be used in addition to antigens specific to a target of interest. In some embodiments, a threshold level of detection of the control antigens in a representative human population can be predetermined. In some embodiments, added control antigens (e.g., control peptides) are based on vaccine components that have been used to immunize donors. In some embodiments, control peptides are added to the list of target antigens or query antigens to form a complete set of K antigens/peptides to be assayed (e.g., peptide 1-K can include one or more target peptides and one or more control peptides).

In some embodiments, the counts of LCR chain sequences for control antigens can be used to normalize counts for other antigens to provide comparable figures across PBMC samples. In some embodiments, normalization is accomplished by adjusting the LCR chain sequence counts in a given sample for an antigen to be presented as a ratio of the antigen's counts divided by the sum of the control antigen counts.

Correcting for Experimental Noise

In some embodiments, antigens are distributed into antigen pools based on a minimum Hamming distance between the binary encoding of pools where they reside as described in this disclosure (e.g., using a Hamming(7,4) code; see FIG. 1). In some embodiments, codes for asymmetric channels can be used when the chance of a "1" occurring by error is higher than the chance of a "0" occurring by error such as when a T cell recognizes more than one antigen (see Kim and Freiman, 1959, for examples of asymmetric codes). In some embodiments, other error correcting codes can be employed.

Determining LCR Chain Sequences Specific for Expansion after Antigen Exposure

Figure 3:
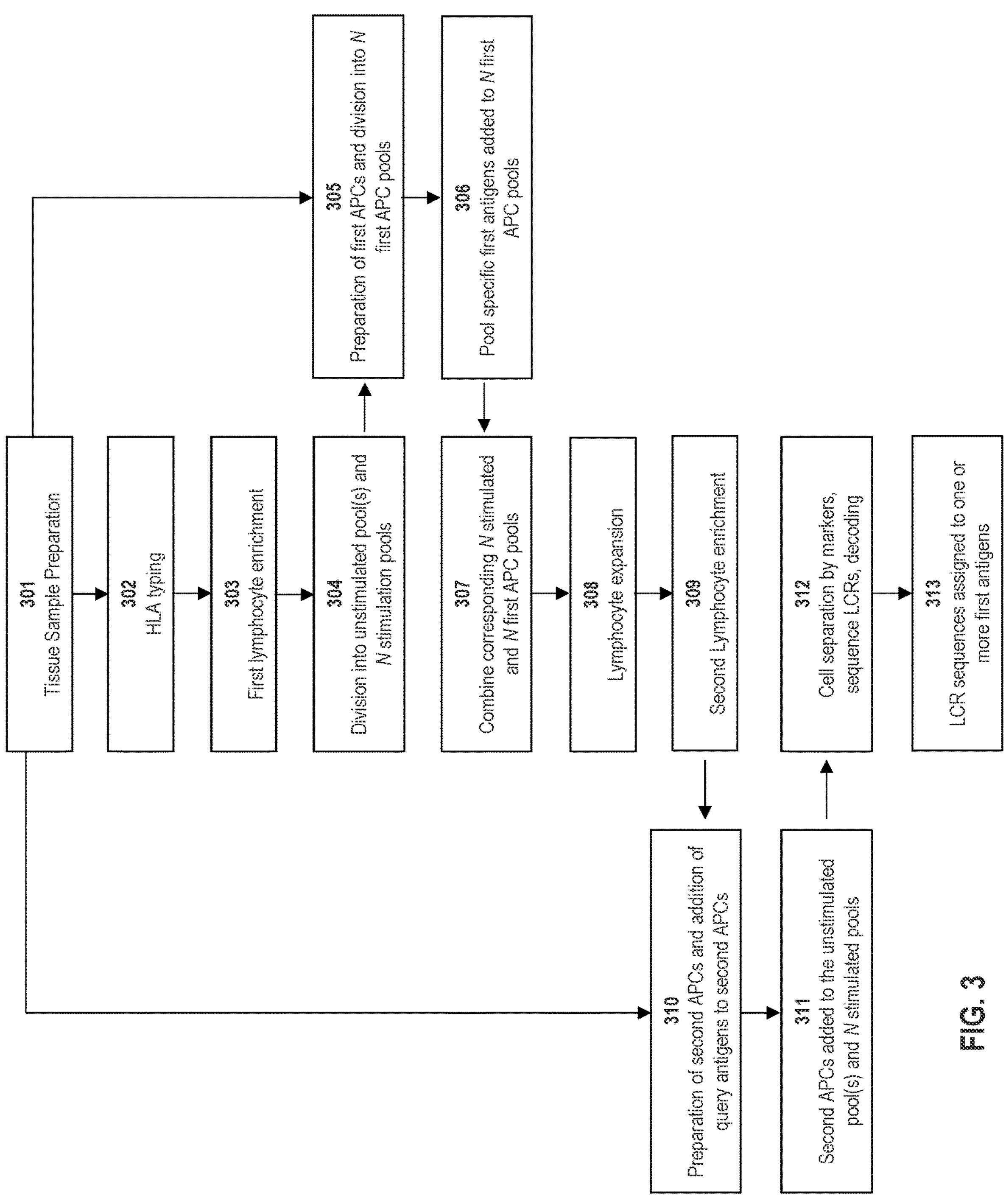
FIG. 3 illustrates a flow chart of detection of lymphocytes that are expanded by exposure to one or more identified first antigens and are activated by one or more query antigens.

In some embodiments, FIG. 3 shows a method of determining one or more LCR chain sequences associated with lymphocytes that are expanded by one or more identified first antigens, where the lymphocytes are subsequently activated by one or more query antigens. In some embodiments, at least one of the query antigens and first antigens are not identical. In some embodiments, a tissue sample (e.g., PBMCs) is prepared at step 301. In some embodiments, the tissue sample is then HLA typed at step 302 to determine the predicted display of antigens by the MHC molecules present in the tissue sample. In some embodiments, the HLA typing at step 302 is used to determine the pool specific first antigens and query antigens that are used based upon their predicted or known display by MHC molecules. In some embodiments, at step 303, lymphocytes (e.g., B cells, CD4+ T cells, and/or CD8+ T cells, or any other desired set of lymphocytes or lymphocyte combinations) are enriched (first lymphocyte enrichment) from a portion of the tissue sample from step 301 using negative magnetic bead selection, or other methods as are known in the art including methods described in Dagur et al. (2015) "Collection, Storage, and Preparation of Human Blood Cells." Curr Protoc Cytom. 2015 Jul. 1; 73:5.1.1-5.1.16, which is incorporated by reference in its entirety herein. In embodiments in which step 303 is performed, the output of step 303 (enriched lymphocytes) is divided into one or more unstimulated pools (i.e., one or more control pools) and N stimulated pools at step 304. In some embodiments, step 303 is omitted, and the method proceeds directly to step 304 where the output of step 301 (tissue sample preparation) is divided into unstimulated pool(s) (i.e., control pool(s)) and N stimulated pools at step 304. In some embodiments, in step 305, first antigen presenting cells (APCs) are prepared from the tissue sample at step 301 using various methods such as those described by Schanen et al. (2008) "A novel approach for the generation of human dendritic cells from blood monocytes in the absence of exogenous factors." *J Immunol Methods.* 2008 Jun. 1; 335(1-2):53-64, and Moser et. al. (2010) "Optimization of a dendritic cell-based assay for the in vitro priming of naïve human CD4+ T cells." *J Immunol Methods.* 2010 Feb. 28; 353(1-2):8-19, each of which are incorporated by reference in their entireties herein. Preparing purified APCs for antigen presentation to lymphocytes can improve the effectiveness of antigen display and of lymphocyte activation by the APCs. In some embodiments, at step 305, the first APCs are divided into a total of N first APC pools. At step 306, pool specific first antigens are added to the N first APC pools, wherein each pool specific first antigen is added to a unique subset of the N first APC pools using the encoding methods described herein. In some embodiments, at step 306, nucleic acid constructs encoding the pool specific first antigens are transfected or virally delivered into the cells in the N first APC pools with the pool selection being accomplished using the encoding strategies described herein. In some embodiments, if the pool specific first antigens are vaccines or proteins, the first APCs (e.g., dendritic cells) are pulsed (e.g., for two hours) in step 306 by the pool specific first antigens and then the first APCs are washed in step 306. In some embodiments, at step 307, the N first APC pools from step 306 are added to the N stimulation pools from step 304 with corresponding numbers (e.g., APC pool 1 is added to simulation pool 1, etc.). In some embodiments, at step 307, the first APCs from step 305 are added to the unstimulated pools from step 304 without exposure to the pool specific first antigens. In some embodiments, when lymphocyte enrichment at step 303 is not used, the unstimulated pools and N stimulation pools at step 304 will already contain APCs (e.g., dendritic cells) and thus steps 305 and 306 are eliminated and each pool specific first antigen is added directly to a unique subset of the N simulation pools at step 307 using the encoding methods described herein. In some embodiments, control antigens (e.g., a CAP1 peptide or other known MHC class I or class II control peptides) are added to all pools at step 307. In some embodiments, control antigens are added to the first APCs at step 305. In some embodiments, the control antigens are selected based upon the HLA typing from step 302.

As shown in FIG. 3, at step 308, the lymphocytes from step 307 are allowed to expand. In some embodiments, typical expansion times are 10 to 12 days, and typical culture expansion conditions are described by Tapia-Calle et al. (2019) and Schanen et al. (2011) "Coupling sensitive in vitro and in silico techniques to assess cross-reactive CD4(+) T cells against the swine-origin H1N1 influenza virus." Vaccine. 2011 Apr. 12; 29(17):3299-309 each of which are incorporated by reference in their entireties herein. In some embodiments, multiple rounds of in vitro stimulation are used that repeat steps 305-308 to expand rare lymphocytes, for example using the in vitro simulation cycle method described in Abrams et al. (1997) "Generation of stable CD4+ and CD8+ T cell lines from patients immunized with ras oncogene-derived peptides reflecting codon 12 mutations." Cell Immunol. 1997 Dec. 15; 182(2):137-51, incorporated by reference in its entirety herein. In some embodiments, the enrichment of lymphocytes activated by the control antigens added at step 305 or step 307 is monitored to determine the number of rounds of in vitro stimulation required.

As shown in FIG. 3, after lymphocyte expansion at step 308, in some embodiments, desired lymphocytes are enriched at step 309 (second lymphocyte enrichment step) using negative magnetic bead selection, or other methods as described herein. In some embodiments, step 309 is omitted and lymphocytes are not enriched after they have undergone expansion at step 308. In some embodiments, second APCs are prepared fresh in step 310 from the tissue sample at step 301 as described herein, the second APCs are added into a single pool and the query antigens are added to this single pool of second APCs. In some embodiments, if the query antigens are vaccines or proteins, at step 310 the second APCs are pulsed (e.g., for two hours) and the second APCs are then washed. In some embodiments, at step 310, nucleic acid constructs encoding the query antigens are transfected or virally delivered into the second APCs. In some embodiments, at step 311, the second APCs, after antigen addition in step 310, are added to the unstimulated pool(s) and N stimulated pools. In some embodiments, at step 311, the query antigens are all added directly to the unstimulated pool(s) and to the N stimulated pools along with output of second APC preparation from step 310. In some embodiments, when lymphocyte enrichment at step 309 is not used, the unstimulated pool(s) and N stimulated pools will already contain APCs (e.g., dendritic cells) and step 310 is eliminated and at step 311, all query antigens are added directly to the one or more unstimulated pool(s) and N simulation pools. At step 312, cells in the resulting pools are given time to activate and then each pool is separated by markers for activated and non-activated lymphocytes of a desired type, the LCR chains in each pool specific fraction are sequenced, and the decoding algorithm described herein is used to assign, at step 313, LCR chain sequences to one or more first antigens based upon their expansion of lymphocytes that were subsequently activated by query antigens. In some embodiments, the enrichment of LCR chain sequences in the N stimulated pools utilizes the LCR chain sequence read counts or cell counts observed for the same LCR chain sequence in the unstimulated pool(s), and the detection of an enriched LCR chain sequence of a lymphocyte that recognizes a first antigen in one or more of the N stimulation pools is based upon its relative read count or cell count when compared to the unstimulated pool(s). This enrichment is then used for decoding one or more pool specific first antigens as described herein. This LCR chain sequence enrichment corresponds to a lymphocyte that is activated by at least one of the query antigens in addition to the one or more first antigens that are decoded. Thus, these LCR chain sequences recognize both the one or more first antigens decoded and at least one of the query antigens.

Figure 4:
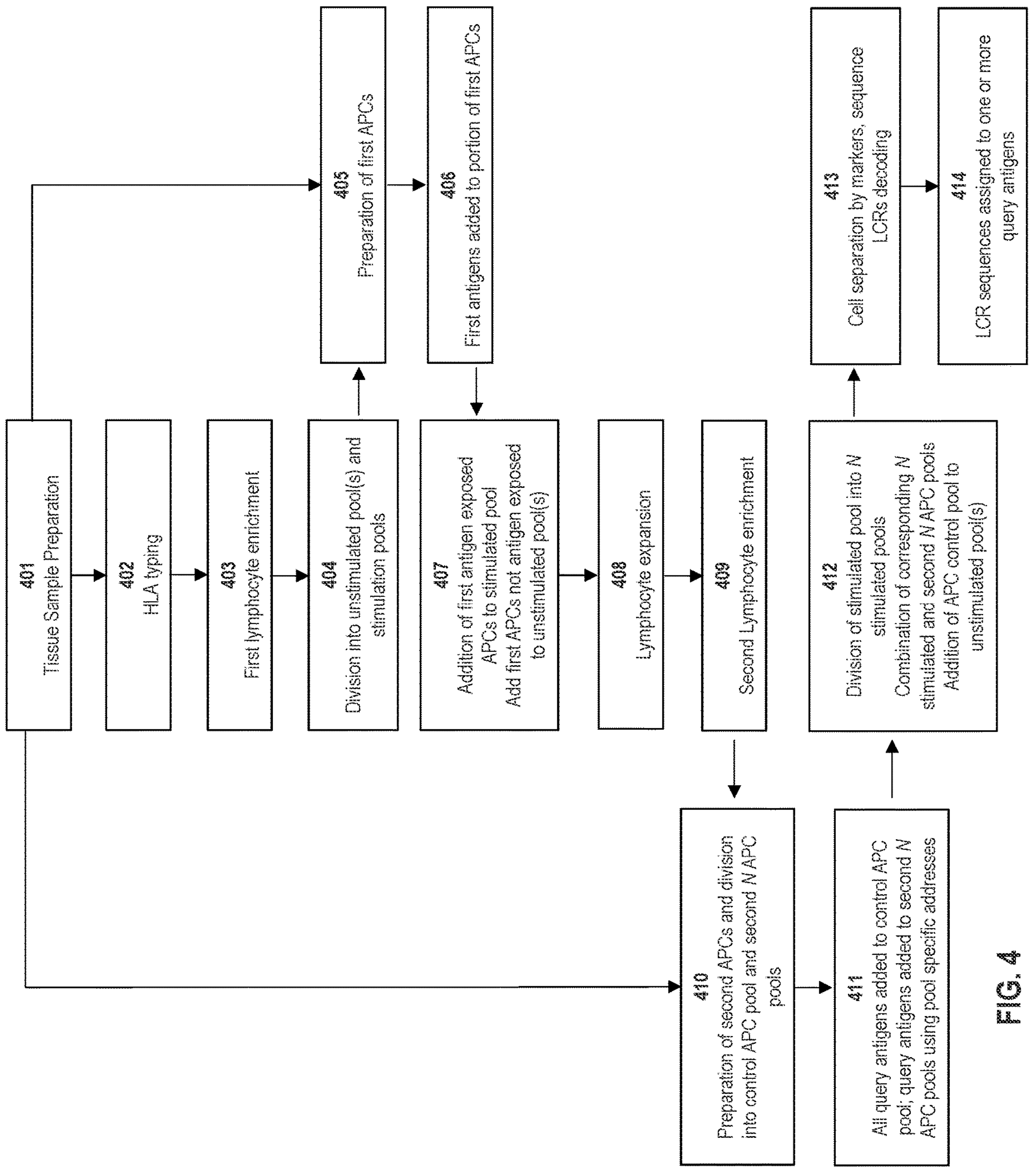
FIG. 4 illustrates a flow chart of detection of lymphocytes that are expanded by exposure to one or more first antigens and are activated by one or more identified query antigens.

In alternate embodiments, referring to FIG. 4, a method is described for determining one or more LCR chain sequences associated with lymphocytes that are activated by one or more identified query antigens, where the lymphocytes have been previously expanded by one or more first antigens. In some embodiments, at least one of the query antigens and first antigens are not identical. In some embodiments, a tissue sample (e.g., PBMCs) is prepared at step 401 and is HLA typed at step 402 to determine the predicted display of antigens by the MHC molecules present in the tissue sample. In some embodiments, the HLA typing from step 402 is used to determine the first antigens and query antigens that are used based upon their predicted or known display by MHC molecules. In some embodiments, lymphocytes (e.g., B cells, CD4+ T cells, and/or CD8+ T cells, or any other desired set of lymphocytes or lymphocyte combinations) are enriched from a portion of the tissue sample at step 403 using negative magnetic bead selection, or other methods including methods described in Dagur et al. (2015). In some embodiments, the tissue sample is used directly without lymphocyte enrichment and step 403 is omitted. In some embodiments, at step 404, the output of step 403 is divided into one or more unstimulated pools (i.e., one or more control pools) and a stimulated pool. In some embodiments, at step 405, APCs are prepared from the tissue sample from step 401 using, for example, the methods described by Schanen et al. (2008) and Moser et. al. (2010). Preparing purified APCs for antigen presentation to lymphocytes can improve the effectiveness of antigen display and of lymphocyte activation by the APCs. In some embodiments, at step 406, the APCs from step 405 are divided into a control APC pool (not exposed to first antigens) and a first antigen exposed APC pool. The first antigens are then added to the first antigen exposed APC pool. In some embodiments, at step 406, if the first antigens are vaccines or proteins, the antigen exposed APC fraction of cells are pulsed (e.g., for two hours) with the first antigens and then washed. In some embodiments, at step 406, nucleic acid constructs encoding the first antigens are transfected or virally delivered into the antigen exposed fraction of APCs. In some embodiments, at step 407, the first antigen exposed APCs from step 406 are added to the stimulated pool from step 404. In some embodiments, at step 407, the control APC pool (not exposed to first antigen) from step 406 are added to the unstimulated pool(s) from step 404. In some embodiments, at step 407, the first antigens are added directly to the stimulated pool from step 404 along with output of APC preparation from step 405. In some embodiments, when lymphocyte enrichment at step 403 is not used, the unstimulated (i.e., control) and stimulation pools from step 404 will already contain APCs (e.g., dendritic cells) and step 405 and 406 are eliminated and the first antigens are added directly to the N simulation pools from step 404. In some embodiments, control antigens (e.g., a CAP1 peptide or other known MHC class I or class II control peptides) are added to all pools at step 407. In some embodiments, control antigens are added to the first APCs at step 405. In some embodiments, the control antigens are selected based upon the HLA typing from step 402.

As shown in FIG. 4, at step 408, the lymphocytes from step 407 are allowed to expand. In some embodiments, typical expansion times are 10-12 days, and typical culture expansion conditions are described by Tapia-Calle et al. (2019) and Schanen et al. (2011). In some embodiments, multiple rounds of in vitro stimulation are used that repeat steps 405, 406, and 407 to expand rare lymphocytes, for example using the in vitro simulation cycle method described in Abrams et al. (1997) "Generation of stable CD4+ and CD8+ T cell lines from patients immunized with ras oncogene-derived peptides reflecting codon 12 mutations." Cell Immunol. 1997 Dec. 15; 182(2):137-51, incorporated in its entirety herein. In some embodiments, the enrichment of lymphocytes activated by the control antigens added at step 405 or 407 is monitored to determine the number of rounds of in vitro stimulation required.

As shown in FIG. 4, after lymphocyte expansion, in some embodiments, desired lymphocytes are enriched at step 409 using negative magnetic bead selection, or other methods as described above. In some embodiments, step 409 is omitted and lymphocytes are not enriched after they have undergone expansion at step 408. In some embodiments, fresh second APCs are prepared at step 410 from the tissue sample prepared at step 401 as described herein, and the second APCs are split into second control APC and second N APC pools. In some embodiments, at step 411, pool specific query antigens are encoded and placed into the second N APC pools as described by the methods herein. In some embodiments, all of the pool specific query antigens are added to the second control pool of APCs from step 410 to test the unstimulated pool(s) for lymphocyte activation that is independent of first antigen stimulation. In some embodiments, at step 411, if the query antigens are vaccines or proteins, the APCs are pulsed (e.g., for two hours) in their respective pools and then the APCs are washed. At step 412, the simulated pool is divided into N stimulated pools. In some embodiments, at step 412, the antigen exposed second N APC pools from step 411 are added to these N stimulation pools with corresponding numbers (e.g., second APC pool 1 is added to simulation pool 1, etc.). In some embodiments, at step 412, the second control APC pools (exposed to the query antigens) from step 411 are added to the unstimulated pool(s). In some embodiments, when lymphocyte enrichment at step 409 is not used, the output of step 408 will already contain APCs (e.g., dendritic cells), steps 410 and 411 are omitted, and at step 412, pool specific query antigens are added to the unstimulated and N stimulated pools created by step 412 with pool selection for each antigen accomplished using the encoding methods described herein. At step 413, the lymphocytes are given time to activate, and then each pool is separated by markers for activated and non-activated lymphocytes of a desired type, the LCR chains in each pool specific fraction are sequenced, and the decoding algorithm described herein is used to assign LCR chain sequences to one or more query antigens that activate lymphocytes that were expanded by the set of first antigens. In some embodiments, the enrichment of LCR chain sequences in the N simulated pools utilizes the LCR chain sequence read counts or cell counts observed for the same LCR chain sequence in the unstimulated pool(s), and the detection of an enriched LCR chain sequence of a lymphocyte that recognizes a query antigen in one or more of the N stimulation pools is based upon its increased read count or cell count when compared to the unstimulated pool(s). This enrichment is then used for decoding one or more pool specific query antigens as described herein. This LCR chain sequence enrichment corresponds to a lymphocyte that is expanded by at least one of the first antigens in addition to the one or more query antigens that are decoded. Thus, these LCR chain sequences recognize both the one or more query antigens decoded and at least one of the first antigens.

Additional Methods for the Stimulation of Antigen Presenting Cells with Antigens In some embodiments, APCs or APCs mixed with other cell types (e.g., as in PBMCs isolated from an individual) can be stimulated with a vaccine that consists of one or more antigens that are physically associated (e.g., covalent coupled) to a VHH domain that binds to cells that have MHC class II molecules on their surface. In some embodiments, a VHH targeting domain is any VHH domain that competes for binding to MHC class II complexes HLA-DR1, HLA-DR2, and HLA-DR4 with a VHH comprising SEQ ID NO: 1 or SEQ ID NO: 2. One example of this method of APC simulation is described in U.S. Pat. No. 9,751,945 which is incorporated herein in its entirety. In some embodiments, VHH targeting domains are VHH molecules that bind to cell surface proteins of antigen presenting cells (e.g., DEC-205). In some embodiments, VHH targeting domains are VHH molecules that bind to cell surface proteins present on cells that have MHC class II molecules on their surface. In some embodiments, VHH targeting domains are VHH molecules that bind to cell type specific surface proteins (e.g., CD4). In some embodiments, antigens physically associated with VHH targeting domains are used in one or more of the following steps: steps 306 and 311 of FIG. 3, as well as steps 406 and 411 of FIG. 4. Examples of VHH targeting domains are SEQ ID NO: 1 and SEQ ID NO: 2. In some embodiments, VHH targeting domains are joined to antigens with linker sequences including fusion protein linkers described in Chen et al. (2012) "Fusion protein linkers: property, design and functionality." *Advanced Drug Delivery Reviews* 65.10 (2013): 1357-1369. PMID 23026637, which is incorporated by reference in its entirety herein. In some embodiments, linker sequences appear before an antigen. In some embodiments, linker sequences appear after an antigen. GGSGGGGSGG (SEQ ID NO: 3) is an example linker sequence. In some embodiments, antigens are natively occurring epitopes, such as the KRAS neoantigens LVVVGADGV (SEQ ID NO: 5) and EYKLVVVGADGVG (SEQ ID NO: 7). In some embodiments, antigens are heteroclitic derivatives of naturally occurring epitopes as described by U.S. Pat. No. 11,058,751, which is incorporated in its entirety herein. In some embodiments, a vaccine comprises one or more heteroclitic antigens that are physically associated with a VHH targeting domain. For example, LMVVGADGV (SEQ ID NO: 4) is a heteroclitic derivative of LVVVGADGV (SEQ ID NO. 5), and EYKFVVFGSDGAG (SEQ ID NO: 6) is a heteroclitic derivative of EYKLVVVGADGVG (SEQ ID NO: 7). An example of a VHH targeting domain (SEQ ID NO: 1) that is combined with a linker (SEQ ID NO: 3) and the single heteroclitic antigen LMVVGADGV (SEQ ID NO: 4) is SEQ ID NO: 8.

```
                                             (SEQ ID NO: 8)
QVQLQESGGGLVQAGGSLRLSCAASGSTLSSYGMGWYRQAPGKQREVVA

TISATGSISYADSVKGRFTISRDSAKNTMYLQLNSLTPEDTAVYYCNTI

YRSTLYWGQGTQVTVSSGGSGGGGSGGLMVVGADGV.
```

An example of a VHH targeting domain (SEQ ID NO: 1) that is combined with a linker (SEQ ID NO: 3), the heteroclitic antigen LMVVGADGV (SEQ ID NO: 4), a linker (SEQ ID NO: 3), and the heteroclitic antigen EYKFVVFGSDGAG (SEQ ID NO: 6) is SEQ ID NO: 9.

```
                                             (SEQ ID NO: 9)
QVQLQESGGGLVQAGGSLRLSCAASGSTLSSYGMGWYRQAPGKQREVVA

TISATGSISYADSVKGRFTISRDSAKNTMYLQLNSLTPEDTAVYYCNTI

YRSTLYWGQGTQVTVSSGGSGGGGSGGLMVVGADGVGGSGGGGSGGEYK

FVVFGSDGAG.
```

A VHH-antigen molecule is a single polypeptide vaccine that encodes one or more antigens that are covalently coupled to a VHH targeting domain. Examples of VHH-antigen molecules are SEQ ID NO: 8 and SEQ ID NO: 9. VHH-antigen molecules can be expressed and purified, using for example the methods described in U.S. Pat. No. 9,751,945, which is incorporated herein in its entirety. In some embodiments, a VHH-antigen molecule is encoded as an mRNA molecule that is expressed in vivo, for example in a cell line or in an individual. In some embodiments, the encoding of a VHH-antigen molecule as a mRNA molecule for expression includes a start codon at its beginning. In some embodiments, the encoding of a VHH-antigen molecule as a mRNA molecule includes a secretion signal sequence as described in U.S. Pat. No. 9,751,945, which is incorporated herein in its entirety. In some embodiments, a VHH-antigen mRNA molecule is delivered with an mRNA-LNP formulation as is known in the art. In some embodiments, a vaccine for administration to an individual can be constructed by physically associating (e.g., covalent coupling) one or more antigens to a VHH targeting domain. In some embodiments, a vaccine for administration to an individual can be constructed by physically associating (e.g., covalent coupling) one or more heteroclitic antigens to a VHH targeting domain.

Methods for Producing Collision Free Superimposed Codes

In some embodiments, collision free superimposed codes are used to assign antigens to pools. A collision free superimposed code is defined as a superimposed code that guarantees that each superimposed code word has a unique decoding into one or more antigens. A superimposed code encodes multiple antigens into a single superimposed code word by the logical "OR" of their antigen specific code words. In some embodiments, collision free superimposed codes assume that R antigens are each placed into n pools out of a total of N pools and LCRs only recognize up to r antigens.

Table 2 shows a collision free superimposed code that provides unique code words for 18 antigens (R=18) where each antigen is placed into 4 pools (n=4) out of a total of ten pools (P1-P10) (N=10), and where r is bounded by two (at most two antigens will be recognized by an LCR) (r=2). For example, the superimposed code for antigens 1 and 2 in Table 2 is "1 1 1 0 0 1 1 0 0 1" which does not collide with any other antigen code word (or superimposed code word of two antigens) in Table 2.

TABLE 2

Collision free superimposed code for 18 antigens

| Antigen Number | P1 | P2 | P3 | P4 | P5 | P6 | P7 | P8 | P9 | P10 |
|---|---|---|---|---|---|---|---|---|---|---|
| 1 | 1 | 0 | 1 | 0 | 0 | 1 | 1 | 0 | 0 | 0 |
| 2 | 0 | 1 | 1 | 0 | 0 | 1 | 0 | 0 | 0 | 1 |
| 3 | 0 | 1 | 0 | 0 | 0 | 1 | 1 | 1 | 0 | 0 |
| 4 | 0 | 1 | 0 | 0 | 1 | 0 | 1 | 0 | 1 | 0 |
| 5 | 0 | 0 | 1 | 0 | 1 | 0 | 0 | 0 | 1 | 1 |
| 6 | 0 | 1 | 0 | 1 | 0 | 0 | 0 | 1 | 1 | 0 |
| 7 | 0 | 0 | 0 | 1 | 1 | 1 | 0 | 1 | 0 | 0 |
| 8 | 0 | 0 | 1 | 1 | 1 | 0 | 1 | 0 | 0 | 0 |
| 9 | 1 | 0 | 0 | 1 | 0 | 0 | 1 | 0 | 1 | 0 |
| 10 | 0 | 1 | 0 | 1 | 1 | 0 | 0 | 0 | 0 | 1 |
| 11 | 0 | 0 | 0 | 0 | 1 | 1 | 1 | 0 | 0 | 1 |
| 12 | 0 | 0 | 1 | 0 | 0 | 1 | 0 | 1 | 1 | 0 |
| 13 | 1 | 0 | 1 | 1 | 0 | 0 | 0 | 0 | 0 | 1 |
| 14 | 1 | 1 | 1 | 0 | 0 | 0 | 0 | 0 | 1 | 0 |
| 15 | 1 | 1 | 0 | 0 | 1 | 1 | 0 | 0 | 0 | 0 |
| 16 | 0 | 0 | 0 | 0 | 0 | 0 | 1 | 1 | 1 | 1 |
| 17 | 1 | 0 | 0 | 0 | 1 | 0 | 0 | 1 | 1 | 0 |
| 18 | 0 | 0 | 0 | 1 | 0 | 1 | 0 | 0 | 1 | 1 |

The collision free superimposed code in Table 2 guarantees that any superimposed code word (a single antigen code word, or the logical OR of any two antigen code words) has a unique decoding into its originating one or two antigens. In some embodiments, nearest set decoding as described herein can be used to determine the antigens recognized by an LCR based upon the appearance of the LCR receptor sequence in pools that correspond to a "1" in a superimposed code, and "0" where the LCR receptor sequence does not appear. In some embodiments, LCR receptor sequence appearance in a pool is based upon statistical metrics as described herein.

In some embodiments, collision free superimposed codes are determined by a random search method. First, an antigen is chosen at random to initialize the search. In Step 1, a random code word is chosen for the antigen that is distinct from any previously chosen antigen code word, where the randomly chosen antigen code word has exactly n "1" bits and total length of N bits. In Step 2, all superimposed code words for existing antigens and the new antigen code word for combinations up to r are computed. In Step 3, if any of the superimposed code words computed in Step 2 are the same, then the method returns to Step 1 to pick a replacement antigen code word. In Step 4, the code word for the antigen is recorded, and a new antigen is chosen at random, and the method continues again from Step 1. If at Step 4 all antigens have had code words assigned, then the method has determined a collision free superimposed code. In some embodiments, if at Step 1 all possible remaining code words have been tried for a given antigen, then the method stops with failure for the parameters provided, and the method can be repeated starting over from Step 1. In some embodiments, if a fixed number of random code words selected at Step 1 fail in a row without a new code word being recorded at Step 4, the method stops with failure to find a collision free superimposed code, and the method can be repeated from Step 1. After multiple failed attempts, it is possible that a superimposed code with the given constraints does not exist.

In some embodiments, antigens are arranged into overlap sets, where it is assumed that no LCR can recognize antigens in distinct overlap sets. For example, 30 antigens can be organized into 10 overlap sets of 3 antigens each. In this example, it is assumed that each LCR may recognize a maximum of r antigens in each overlap set. In some embodiments with overlap sets, a collision free superimposed code consists of a prefix code that determines an overlap set, and a suffix code that determines the one or more antigens within this overlap set. A given antigen is placed into pools corresponding to "1" bits in the prefix code for its overlap set, and into pools corresponding to "1" bits in their antigen specific code (the suffix code) within their overlap set.

In some embodiments, the prefix code has one code word for each overlap set. In some embodiments, the prefix code is not a superimposed code. In some embodiments, the prefix code is an error correcting code as described herein. In some embodiments, the prefix code is chosen using the methods described herein with R being the number of overlap sets and r=1. In some embodiments, the number of bits (e.g., pools) for the prefix code is chosen to accommodate an error correcting code that can encode R overlap sets. In some embodiments, the prefix code uses redundancy, such as two pools out of five.

In some embodiments, the suffix code has one code word for each antigen in the largest overlap set. In some embodiments, overlap sets share code words (e.g., the first antigen in each overlap set has the same suffix code word, the second antigen in each overlap set has the same suffix code word, etc.). In some embodiments, the suffix code is a collision free superimposed code with r equal to the assumed maximum number of antigens that are recognized by an LCR within an overlap set. In some embodiments, the number of bits (e.g., pools) for the suffix code is chosen to accommodate the number of antigens in the largest overlap set and the value of r.

Table 3 illustrates a collision free superimposed code for 30 antigens placed into 8 pools where each LCR is assumed to not recognize antigens in distinct overlap sets. A "1" indicates that an antigen is placed into a pool, and a "0" indicates that an antigen is not placed into a pool. The example superimposed code in Table 3 is for 30 antigens organized into 10 overlap sets of 3 antigens per set. A prefix code is used to place the 30 antigens into pools P1 to P5, and a suffix code is used to place the 30 antigens into pools P6 to P8. In this example the prefix code uses a two out of five encoding system. In this example, the suffix code assumes r=3 and thus an LCR can recognize all three of the antigens and three pools are used to encode the suffix code, one pool per overlap set antigen.

TABLE 3

Collision free superimposed code for 30 antigens

| Antigen Number | Over-lap Set | P1 Prefix | P2 Prefix | P3 Prefix | P4 Prefix | P5 Prefix | P6 Suffix | P7 Suffix | P8 Suffix |
|---|---|---|---|---|---|---|---|---|---|
| 1 | 1 | 1 | 1 | 0 | 0 | 0 | 1 | 0 | 0 |
| 2 | 1 | 1 | 1 | 0 | 0 | 0 | 0 | 1 | 0 |
| 3 | 1 | 1 | 1 | 0 | 0 | 0 | 0 | 0 | 1 |
| 4 | 2 | 1 | 0 | 1 | 0 | 0 | 1 | 0 | 0 |
| 5 | 2 | 1 | 0 | 1 | 0 | 0 | 0 | 1 | 0 |
| 6 | 2 | 1 | 0 | 1 | 0 | 0 | 0 | 0 | 1 |
| 7 | 3 | 1 | 0 | 0 | 1 | 0 | 1 | 0 | 0 |
| 8 | 3 | 1 | 0 | 0 | 1 | 0 | 0 | 1 | 0 |
| 9 | 3 | 1 | 0 | 0 | 1 | 0 | 0 | 0 | 1 |
| 10 | 4 | 1 | 0 | 0 | 0 | 1 | 1 | 0 | 0 |
| 11 | 4 | 1 | 0 | 0 | 0 | 1 | 0 | 1 | 0 |
| 12 | 4 | 1 | 0 | 0 | 0 | 1 | 0 | 0 | 1 |
| 13 | 5 | 0 | 1 | 1 | 0 | 0 | 1 | 0 | 0 |
| 14 | 5 | 0 | 1 | 1 | 0 | 0 | 0 | 1 | 0 |
| 15 | 5 | 0 | 1 | 1 | 0 | 0 | 0 | 0 | 1 |
| 16 | 6 | 0 | 1 | 0 | 1 | 0 | 1 | 0 | 0 |
| 17 | 6 | 0 | 1 | 0 | 1 | 0 | 0 | 1 | 0 |
| 18 | 6 | 0 | 1 | 0 | 1 | 0 | 0 | 0 | 1 |
| 19 | 7 | 0 | 1 | 0 | 0 | 1 | 1 | 0 | 0 |
| 20 | 7 | 0 | 1 | 0 | 0 | 1 | 0 | 1 | 0 |
| 21 | 7 | 0 | 1 | 0 | 0 | 1 | 0 | 0 | 1 |
| 22 | 8 | 0 | 0 | 1 | 1 | 0 | 1 | 0 | 0 |
| 23 | 8 | 0 | 0 | 1 | 1 | 0 | 0 | 1 | 0 |
| 24 | 8 | 0 | 0 | 1 | 1 | 0 | 0 | 0 | 1 |
| 25 | 9 | 0 | 0 | 1 | 0 | 1 | 1 | 0 | 0 |
| 26 | 9 | 0 | 0 | 1 | 0 | 1 | 0 | 1 | 0 |
| 27 | 9 | 0 | 0 | 1 | 0 | 1 | 0 | 0 | 1 |
| 28 | 10 | 0 | 0 | 0 | 1 | 1 | 1 | 0 | 0 |
| 29 | 10 | 0 | 0 | 0 | 1 | 1 | 0 | 1 | 0 |
| 30 | 10 | 0 | 0 | 0 | 1 | 1 | 0 | 0 | 1 |

The devices, systems, and methods disclosed herein are not to be limited in scope to the specific embodiments described herein. Indeed, various modifications of the devices, systems, and methods in addition to those described will become apparent to those of skill in the art from the foregoing description.

What is claimed is:

1. A method for determining a lymphocyte receptor chain sequence, or a portion thereof, specific for at least two antigens, the method comprising:

providing a biological sample comprising a plurality of lymphocytes;

extracting a plurality of first antigen presenting cells from the biological sample;

dividing the plurality of first antigen presenting cells into a plurality of first reaction mixtures;

sorting a plurality of first antigens into the plurality of first reaction mixtures, wherein the sorting comprises adding a unique first antigen of the plurality of first antigens to a unique subset of the plurality of first reaction mixtures, and wherein two unique first antigens are not added to any two identical subsets of the plurality of first reaction mixtures;

contacting each first reaction mixture with the biological sample;

providing a condition for a first activated lymphocyte in at least one first reaction mixture of the plurality of first reaction mixtures to expand in number such that a plurality of lymphocyte clones is formed;

extracting a plurality of second antigen presenting cells from the biological sample;

adding the plurality of second antigen presenting cells into a second reaction mixture;

adding a plurality of query antigens into the second reaction mixture;

dividing the second reaction mixture into the plurality of first reaction mixtures to create a plurality of final reaction mixtures;

separating a second activated lymphocyte and a non-activated lymphocyte from a subset of the plurality of final reaction mixtures, wherein the second activated lymphocyte recognizes a query antigen of the plurality of query antigens, wherein the query antigen is different from any antigen of the plurality of first antigens;

sequencing nucleic acids of the second activated lymphocyte to obtain the lymphocyte receptor chain sequence; and detecting the unique first antigen of the plurality of first antigens, wherein the unique first antigen and the query antigen are specific for the lymphocyte receptor chain sequence.

2. The method of claim 1, wherein the first activated lymphocyte is a T cell or a B cell.

3. The method of claim 1, further comprising HLA typing of the biological sample to determine a predicted display of at least one antigen of the plurality of first antigens by an MHC molecule present in the biological sample.

4. The method of claim 1, further comprising enriching the plurality of lymphocytes prior to sorting the plurality of first antigens into the plurality of first reaction mixtures.

5. The method of claim 1, further comprising enriching the plurality of lymphocytes after providing the condition for the first activated lymphocyte to expand in number and prior to extracting the plurality of second antigen presenting cells.

6. The method of claim 1, wherein separating the second activated lymphocyte and the non-activated lymphocyte is performed based on a marker, wherein the marker is selected from the group consisting of CD3, CD4, CD8, CD137, OX40, CD25, PD-L1, CD69, CD154, and a combination thereof.

7. The method of claim 1, wherein the second activated lymphocyte recognizes the query antigen by binding an MHC complex comprising the query antigen.

8. The method of claim 1, wherein the sorting further comprises applying, using a processor, an error-correcting code configured to determine the unique subset of the plurality of first reaction mixtures that the unique first antigen is added to.

9. The method of claim 8, wherein the error-correcting code is a collision free superimposed code configured to allow for detection of at least two unique first antigens specific for the lymphocyte receptor chain sequence.

10. The method of claim 9, wherein the collision free superimposed code is determined by a random search method.

11. The method of claim 9, wherein the collision free superimposed code consists of:

a plurality of prefix codes, wherein a prefix code of the plurality of prefix codes is assigned to the unique first antigen of the plurality of first antigens, wherein the prefix code identifies an overlap set, wherein the prefix code is identical for more than one first antigen of the plurality of first antigens within the overlap set; and a plurality of suffix codes, wherein a suffix code of the plurality of suffix codes is assigned to the unique first antigen of the plurality of first antigens, wherein a combination of the prefix code and the suffix code is distinct for the unique first antigen.

12. The method of claim 1, wherein the detecting comprises applying, using a processor, a decoding algorithm, wherein the decoding algorithm is configured to detect the unique first antigen specific for the lymphocyte receptor chain sequence when the lymphocyte receptor chain sequence is not substantially present in at least one reaction mixture of the unique subset of the plurality of first reaction mixtures.

13. The method of claim 12, wherein the decoding algorithm is a nearest set algorithm.

14. The method of claim 1, wherein separating the second activated lymphocyte and the non-activated lymphocyte from the subset of the plurality of final reaction mixtures is performed using multimer sorting.

15. The method of claim 1, wherein separating the second activated lymphocyte and the non-activated lymphocyte from the subset of the plurality of final reaction mixtures is performed using fluorescence-based sorting.

16. The method of claim 1, wherein separating the second activated lymphocyte and the non-activated lymphocyte from the subset of the plurality of final reaction mixtures is performed using bead-based sorting.

17. The method of claim 1, wherein a number of reaction mixtures corresponding to the unique subset of the plurality of first reaction mixtures is a function of a number of expected unique first antigens that are specific to the lymphocyte receptor chain sequence.

18. The method of claim 1, wherein the plurality of first reaction mixtures comprises at least one control reaction mixture, wherein the control reaction mixture does not contain any antigens that are added to the biological sample.

19. The method of claim 1, wherein the detecting further comprises computing a frequency of lymphocytes that express the lymphocyte receptor chain sequence.

* * * * *